(12) United States Patent
Jaroskova et al.

(10) Patent No.: US 7,687,644 B2
(45) Date of Patent: Mar. 30, 2010

(54) ADAMANTYL PYRROLIDIN-2-ONE DERIVATIVES AS 11-BETA HYDROXYSTEROID DEHYDROGENASE INHIBITORS

(75) Inventors: Libuse Jaroskova, Vosselaar (BE); Joannes Theodorus Maria Linders, Eindhoven (NL); Christophe Francis Robert Buyck, Hamme (BE); Louis Jozef Elisabeth Van der Veken, Vosselaar (BE)

(73) Assignee: Janssen Pharmaceutica NV (BE)

( * ) Notice: Subject to any disclaimer, the term of this patent is extended or adjusted under 35 U.S.C. 154(b) by 114 days.

(21) Appl. No.: 11/632,195

(22) PCT Filed: Apr. 29, 2005

(86) PCT No.: PCT/EP2005/051970

§ 371 (c)(1),
(2), (4) Date: Jan. 17, 2007

(87) PCT Pub. No.: WO2005/108361

PCT Pub. Date: Nov. 17, 2005

(65) Prior Publication Data

US 2007/0287743 A1 Dec. 13, 2007

(30) Foreign Application Priority Data

May 7, 2004 (EP) ................... 04101993

(51) Int. Cl.
*C07D 207/00* (2006.01)
*A61K 31/40* (2006.01)
(52) U.S. Cl. ...................... 548/543; 514/424
(58) Field of Classification Search ............... None
See application file for complete search history.

(56) References Cited

U.S. PATENT DOCUMENTS

| 6,194,406 | B1 | 2/2001 | Kane et al. |
| 6,211,199 | B1 | 4/2001 | Kane et al. |
| 2001/0034343 | A1 | 10/2001 | Maynard et al. |

FOREIGN PATENT DOCUMENTS

| WO | WO 97/19074 A | 5/1997 |
| WO | WO 97/22604 A | 6/1997 |
| WO | WO 03/065983 A | 8/2003 |
| WO | WO 03/104207 A | 12/2003 |

OTHER PUBLICATIONS

Amgen—Investors—Pipeline; http://www.amgen.com/investors/pipe_AMG221.html (1 page).*
Apria—Resources—News; http://www.apria.com/resources/1,2725,494-769212,00.html (4 pages).*
Pharmas-Cutting-Edge; http://pharmaweblog.com/blog/category/rd/preclinical (1 page).*
Badman et al., Science, 307 (2005), 1909-1914.*
Treatment of Dementia: ANything New?; http://www.medscape.com/viewarticle/547499_print (8 pages).*
Aicher et al., caplus an 2006:440111.*
Amgen - Investors - Pipeline; http://www.amgen.com/investors/pipe_AMG221.html (1 page, 2008).*
Apria - Resources - News; http://www.apria.com/resources/1,2725,494-769212,00.html (4 pages, 2008).*
Pharmas-Cutting-Edge; http://pharmaweblog.com/blog/category/rd/preclinical (1 page, 2006).*
Treatment of Dementia: ANything New?; http://www.medscape.com/viewarticle/547499_print (8 pages, 2006).*

(Continued)

*Primary Examiner*—Golam M. M. Shameem
*Assistant Examiner*—Sun Jae Y Loewe
(74) *Attorney, Agent, or Firm*—Jeremy K. McKown

(57) ABSTRACT

(I)

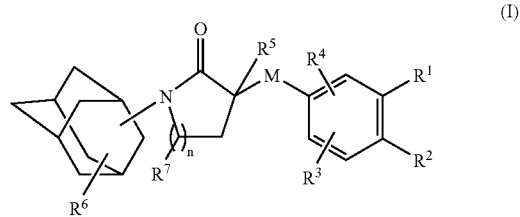

the N-oxide forms, the pharmaceutically acceptable addition salts and the stereochemically isomeric forms thereof, wherein n is 1 or 2;

M represents a direct bond or a $C_{1-3}$alkyl linker optionally substituted with one or two substituents selected from $C_{1-4}$alkyl, $C_{1-3}$alkyloxy-$C_{1-4}$alkyl-, hydroxy-$C_{1-4}$alkyl-, hydroxy, $C_{1-3}$alkyloxy- or phenyl-$C_{1-4}$alkyl-;

$R^1$ and $R^2$ each independently represent hydrogen, halo, cyano, hydroxy, $C_{1-4}$alkyl optionally substituted with halo, $C_{1-4}$alkyloxy-optionally substituted with one or where possible two or three substituents selected from hydroxy, $Ar^1$ and halo;

$R^3$ represents hydrogen, halo, $C_{1-4}$alkyl, $C_{1-4}$alkyloxy-, cyano or hydroxy;

$R^4$ represents hydrogen, halo, $C_{1-4}$alkyl, hydroxy, cyano or $C_{1-4}$alkyloxy-optionally substituted with one or where possible two or three substituents selected from hydroxy and halo;

$R^5$ represents hydrogen, $C_{1-4}$alkyl or $Ar^2$—$C_{1-4}$alkyl-;

$R^6$ represents hydrogen, hydroxy, halo, $C_{1-4}$alkyl or $C_{1-4}$alkyoxy-;

$R^7$ represents hydrogen or $R^7$ and $R^5$ taken together with the carbon atom to which they are attached from a —$C_2$-alkyl-linker;

$Ar^1$ and $Ar^2$ each independently represent phenyl or naphtyl wherein said phenyl and naphtyl are optionally substituted with $C_{1-4}$alkyl, $C_{1-4}$alkyloxy-, or phenyl-$C_{1-4}$ alkyl.

7 Claims, No Drawings

OTHER PUBLICATIONS

International Search Report for PCT/EP2005/051970 dated Jul. 28, 2005.
Division of Medicinal Chemistry Abstracts-234th ACS National Meeting Boston, MA Aug. 19-23, 2007.
Boyle, Craig D., "Recent advances in the discovery of 11β-HSD1 inhibitors.", Current Opinion In Drug Discovery & Development, 2008, 11(4), pp. 495-511, The Thompson Corporation.
Chapman et al., "11β-HSD1, Inflammation, Metabolic Disease and Age-related Cognitive (dys)Function.", Neurochemical Research, 2008, pp. 624-636, vol. 33, Springer Science+Business Media.
Hughes et al., "11-Beta-hydroxysteroid dehydrogenase type 1 (11β-HSD1) inhibitors in Type 2 diabetes mellitus and obesity.", Expert Opinion. Investig. Drugs, 2008, pp. 481-496, vol. 17, (4), Informa Healthcare, UK.
Wamil et al., "Inhibition of 11β-hydroxysteroid dehydrogenase type 1 as a promising therapeutic target.", Drug Discovery Today, Jul. 2007, pp. 504-520, vol. 12, (13/14), Elsevier.
Yau et al., "Targeting 11β-hydroxysteroid dehydrogenase type 1 in brain: therapy for cognitive aging?", Expert Review of Endrocrinology & Metabolism, 2006, pp. 527-536, vol. 1, (4), Future Drugs Ltd.
"Incyte's Selective Oral Inhibitor of 11beta-HSD1 Demonstrates Improvements in Insuling Sensitivity and Lowers Cholesterol levels in Type 2 Diabetics." About Incyte: Press Release, Incyte Corporation website, http://investor.incyte.com, Jun. 9, 2008.
Aicher et al., "Kappa Opioid Receptor (KOR) and GAD67 Immunoreactivity Are Found in Off and Neutral Cells in the Rostral Ventromedial Medulla.", J. Neurophysiol, 2006, vol. 96, pp. 3465-3473, Caplus an 2006:440111.
Baussane et al., "Asymmetric synthesis of 3-substituted pyrrolidones via α-alkylation of a chiral non-racemic γ-lactam.", Tetrahedron: Asymmetry, 1998, vol. 9(5), pp. 797-804.
Blommaert et al., "Mono and Sequential BIS Solid Phase Alkylations Of A (R)-Phenylglycinol Derived Pyrrolidinone Scaffold.", Heterocycles, 2001, vol. 55(12), pp. 2273-2278.
Masuzaki et al., "A Transgenic Model of Visceral Obesity and the Metabolic Syndrome.", Science, 2001, vol. 294, pp. 2166-2170.
Montague et al., "Perspective in Diabetes. The Perils of Portliness. Causes and Consequences of Visceral Adiposity.", Diabetes, 2000, vol. 49, pp. 883-888.
Rauz et al., "Expression and Putative Role of 11β-Hydroxysteroid Dehydrogenase Isozymes within the Human Eye.", Invest. Ophtalmol. Vis. Science, Aug. 2001, vol. 42(9), pp. 2037-2042.
Stewart et al., "Cortisol, 11β-hydroxysteroid dehydrogenase type 1 and central obesity.", Trends. Endrocrin. Metabol., 2002, vol. 13, pp. 94-96.
Zhou et al., "Glucocorticoid effects on extracellular matrix proteins and integrins in bovine trabecular meshwork cells in relation to glaucoma.", Int. J. Mol. Med., 1998, vol. 1, pp. 339-346.

* cited by examiner

ADAMANTYL PYRROLIDIN-2-ONE DERIVATIVES AS 11-BETA HYDROXYSTEROID DEHYDROGENASE INHIBITORS

CROSS REFERENCE TO RELATED APPLICATIONS

This application is the national stage of Application No. PCT/EP2005/051970, filed Apr. 29, 2005, which application claims priority from European Patent Appl. No. 04101993.6, filed May 7, 2004.

The metabolic syndrome is a disease with increasing prevalence not only in the Western world but also in Asia and developing countries. It is characterised by obesity in particular central or visceral obesity, type 2 diabetes, hyperlipidemia, hypertension, arteriosclerosis, coronary heart diseases and eventually chronic renal failure (C. T. Montague et al. (2000), Diabetes, 49, 883-888).

Glucocorticoids and 11β-HSD1 are known to be important factors in differentiation of adipose stromal cells into mature adipocytes. In the visceral stromal cells of obese patients, 11β-HSD1 mRNA level is increased compared with subcutaneous tissue. Further, adipose tissue over-expression of 11β-HSD1 in transgenic mice is associated with increased corticosterone levels in the adipose tissue, visceral obesity, insulin sensitivity, Type 2 diabetes, hyperlipidemia and hyperphagia (H. Masuzaki et al (2001), Science, 294, 2166-2170). Therefore, 11β-HSD1 is most likely be involved in the development of visceral obesity and the metabolic syndrome.

Inhibition of 11β-HSD1 results in a decrease in differentiation and an increase in proliferation of adipose stromal cells. Moreover, glucocorticoid deficiency (adrenalectomy) enhances the ability of insulin and leptin to promote anorexia and weight loss, and this effect is reversed by glucocorticoid administration (P. M. Stewart et al (2002), Trends Endocrin. Metabol, 13, 94-96). These data suggest that enhanced reactivation of cortisone by 11β-HSD1 may exacerbate obesity and it may be beneficial to inhibit this enzyme in adipose tissue of obese patients.

Obesity is also linked to cardiovascular risks. There is a significant relationship between cortisol excretion rate and HDL cholesterol in both men and women, suggesting that glucocorticoids regulate key components of cardiovascular risk. In analogy, aortic stiffness is also associated with visceral adiposity in older adults.

Glucocorticoids and Glaucoma

Glucocorticoids increase the risk of glaucoma by raising the intraocular pressure when administered exogenously and in certain conditions of increased production like in Cushing's syndrome. Corticosteroid-induced elevation of intra ocular pressure is caused by increased resistance to aqueous outflow due to glucocorticoid induced changes in the trabecular meshwork and its intracellular matrix. Zhou et al. (Int J Mol Med (1998) 1, 339-346) also reported that corticosteroids increase the amounts of fibronectin as well as collagen type I and type IV in the trabecular meshwork of organcultured bovine anterior segments.

11β-HSD1 is expressed in the basal cells of the corneal epithelium and the non-pigmented epithelial cells. Glucocorticoid receptor mRNA was only detected in the trabecular meshwork, whereas in the non-pigmented epithelial cells mRNA for the glucocorticoid-, mineralocorticoid receptor and 11β-HSD1 was present. Carbenoxolone administration to patients resulted in a significant decrease in intra-ocular pressure (S. Rauz et al. (2001), Invest. Ophtalmol. Vis. Science, 42, 2037-2042), suggesting a role for HSD1-inhibitors in treating glaucoma.

Accordingly, the underlying problem to be solved by the present invention was to identify potent 11β-HSD inhibitors, with a high selectivity for 11β-HSD1, and the use thereof in treating pathologies associated with excess cortisol formation such as obesity, diabetes, obesity related cardiovascular diseases, and glaucoma. As shown hereinbelow, the 3-substituted 2-pyrrolidinone derivatives of formula (I) were found to be useful as a medicine, in particular in the manufacture of a medicament for the treatment of pathologies associated with excess cortisol formation.

Blommaert A. et al. (Heterocycles (2001), 55(12), 2273-2278) provides the preparation of piperidine- and pyrrolidinone-like polymer supported (R)-phenylglycinol-derived scaffolds and in particular discloses 2-Pyrrolidinone, 1-[(1R)-2-hydroxy-1-phenyl-ethyl]-3-methyl-3-(phenylmethyl)- and 2-Pyrrolidinone, 1-[(1R)-2-hydroxy-1-phenylethyl]-3-(phenylmethyl)-, (3R).

Bausanne I. et al. (Tetrahedron: Assymetry (1998), 9(5), 797-804) provides the preparation of 3-substituted pyrrolidinones via α-alkylation of a chiral non-racemic γ-lacton and in particular discloses 1-(2-hydroxy-1-phenylethyl)-3-benzylpyrrolidin-2-one.

US 2001/034343; U.S. Pat. No. 6,211,199; U.S. Pat. No. 6,194,406; WO 97/22604 and WO 97/19074 are a number of patent applications filed by Aventis Pharmaceuticals Inc. providing 4-(1H-benzimidazol-2-yl)[1,4]diazepanes useful for the treatment of allergic diseases. In these applications the 3-substituted pyrrolidinones of the present invention are disclosed as intermediates in the synthesis of said 4-(1H-benzimidazol-2-yl)-[1,4]diazepanes. These applications in particular disclose; 2-Pyrrolidinone, 3-[(4-fluorophenyl) methyl]-1-[(1S)-1-phenylethyl]- and 2-Pyrrolidinone, 3-[(4-fluorophenyl)methyl]-1-[(1R)-1-phenylethyl]-.

However, in none of the cited documents the therapeutic application of the 3-substituted 2-pyrrolidinone derivatives of the present invention has been disclosed. Accordingly, in a first aspect this invention concerns compounds of formula (I)

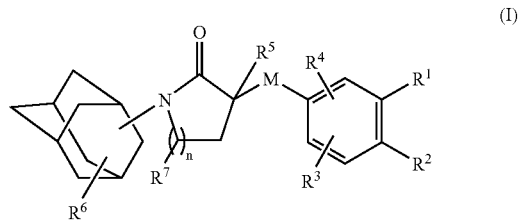

(I)

the N-oxide forms, the pharmaceutically acceptable addition salts and the stereochemically isomeric forms thereof, wherein n is 1 or 2;

M represents a direct bond or a $C_{1-3}$alkyl linker optionally substituted with one or two substituents selected from $C_{1-4}$alkyl, $C_{1-3}$alkyloxy-$C_{1-4}$alkyl-, hydroxy-$C_{1-4}$alkyl-, hydroxy, $C_{1-3}$alkyloxy- or phenyl-$C_{1-4}$alkyl-;

$R^1$ and $R^2$ each independently represent hydrogen, halo, cyano, hydroxy, $C_{1-4}$alkyl optionally substituted with halo, $C_{1-4}$alkyloxy-optionally substituted with one or where possible two or three substituents selected from hydroxy, $Ar^1$ and halo;

R³ represents hydrogen, halo, $C_{1-4}$alkyl, $C_{1-4}$alkyloxy-, cyano or hydroxy;

R⁴ represents hydrogen, halo, $C_{1-4}$alkyl, hydroxy, cyano or $C_{1-4}$alkyloxy-optionally substituted with one or where possible two or three substituents selected from hydroxy and halo;

R⁵ represents hydrogen, $C_{1-4}$alkyl or Ar²—$C_{1-4}$alkyl-;

R⁶ represents hydrogen, hydroxy, halo, $C_{1-4}$alkyl or $C_{1-4}$alkyloxy-;

R⁷ represents hydrogen or R⁷ and R⁵ taken together with the carbon atom to which they are attached from a —$C_2$-alkyl-linker;

Ar¹ and Ar² each independently represent phenyl or naphtyl wherein said phenyl and naphtyl are optionally substituted with $C_{1-4}$alkyl, $C_{1-4}$alkyloxy-, or phenyl-$C_{1-4}$ alkyl.

As used in the foregoing definitions and hereinafter, halo is generic to fluoro, chloro, bromo and iodo; $C_{1-3}$alkyl defines straight and branched chain saturated hydrocarbon radicals having from 1 to 3 carbon atoms such as, for example, methyl, ethyl, propyl, 1-methylethyl and the like; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like; $C_{1-4}$alkyloxy defines straight or branched saturated hydrocarbon radicals having form 1 to 3 carbon atoms such as methoxy, ethoxy, propyloxy, 1-methylethyloxy and the like; $C_{1-4}$alkyloxy defines straight or branched saturated hydrocarbon radicals having form 1 to 4 carbon atoms such as methoxy, ethoxy, propyloxy, butyloxy, 1-methylethyloxy, 2-methylpropyloxy and the like.

The pharmaceutically acceptable addition salts as mentioned hereinabove are meant to comprise the therapeutically active non-toxic acid addition salt forms, which the compounds of formula (I), are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric; citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I), are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I), as well as the salts thereof, are able to form. Such solvates are for example hydrates, alcoholates and the like.

The term stereochemically isomeric forms as used hereinbefore defines the possible different isomeric as well as conformational forms which the compounds of formula (I), may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I), both in pure form or in admixture with each other are intended to be embraced within the scope of the present invention.

The N-oxide forms of the compounds of formula (I), are meant to comprise those compounds of formula (I) wherein one or several nitrogen atoms are oxidized to the so-called N-oxide.

An interesting group of compounds consists of those compounds of formula (I) wherein one or more of the following restrictions apply:

(i) n is 1 or 2;

(ii) M represents a direct bond or a $C_1$-linker optionally substituted with $C_{1-4}$alkyl, hydroxy or hydroxy-$C_{1-4}$ alkyl; preferably M represents a $C_1$-linker optionally substituted with $C_{1-4}$alkyl, hydroxy or hydroxy-$C_{1-4}$ alkyl; in particular M represents a $C_1$-linker;

(iii) R¹ represents hydrogen, hydroxy, cyano, halo, $C_{1-4}$alkyl, $C_{1-4}$alkyloxy-, $C_{1-4}$alkyl substituted with one or where possible two or three halo substituents or R¹ represents $C_{1-4}$alkyloxy substituted with halo;

(iv) R² represents hydrogen, halo, $C_{1-4}$alkyl or $C_{1-4}$alkyloxy-optionally substituted with one or where possible two or three halo substituents;

(v) R³ represents hydrogen, halo, $C_{1-4}$alkyl, $C_{1-4}$alkyloxy- or $C_{1-4}$alkyl substituted with one or where possible two or three halo substituents;

(vi) R⁴ represents hydrogen, halo or $C_{1-4}$alkyl;

(vii) R⁵ represents hydrogen, $C_{1-4}$alkyl or Ar²—$C_{1-4}$alkyl; in particular hydrogen or methyl;

(viii) R⁶ represents hydrogen or hydroxy, in particular hydrogen;

(ix) R⁷ represents hydrogen or R⁷ and R⁵ taken together with the carbon atom to which they are attached form a —$C_2$-alkyl-linker;

(x) Ar² represents phenyl optionally substituted with $C_{1-4}$alkyloxy-.

Another group of interesting compounds consists of those compounds of formula (I) wherein one or more of the following restrictions apply:

(i) n is 1 or 2;

(ii) M represents a $C_1$-linker;

(iii) R¹ and R² represent hydrogen, $C_{1-4}$alkyl or $C_{1-4}$alkyloxy, in particular methyl or methoxy;

(iv) R³ represents hydrogen or $C_{1-4}$alkyloxy, in particular hydrogen or methoxy;

(v) R⁴ represents hydrogen or halo;

(vi) R⁵ represents hydrogen or $C_{1-4}$alkyl, in particular hydrogen or methyl;

(vii) R⁶ represents hydrogen or hydroxy;

(viii) R⁷ represents hydrogen.

Also of interest are those compounds of formula (I) wherein one or more of the following restrictions apply:

(i) n is 1 or 2;

(ii) M represents a $C_1$-linker;

(iii) R¹ represents hydrogen, $C_{1-4}$alkyl or $C_{1-4}$alkyloxy, in particular methyl or methoxy;

(iv) R² represents hydrogen, $C_{1-4}$alkyl or $C_{1-4}$alkyloxy, in particular hydrogen (v) R³ represents hydrogen or $C_{1-4}$alkyloxy, in particular hydrogen or methoxy;

(vi) R⁴ represents hydrogen or halo;

(vii) R⁵ represents hydrogen or $C_{1-4}$alkyl, in particular hydrogen or methyl;

(viii) R⁶ represents hydrogen or hydroxy;
(ix) R⁷ represents hydrogen.

In a preferred embodiment the compounds of formula (I) are selected from the group consisting of;

3-[(3-methoxyphenyl)methyl]-1-tricyclo[3.3.1.1³,⁷]dec-2-yl-2-pyrrolidinone;
3-[(3,5-dimethoxyphenyl)methyl]-1-tricyclo[3.3.1.1³,⁷]dec-2-yl-2-pyrrolidinone;
3-[(4-methylphenyl)methyl]-1-tricyclo[3.3.1.1³,⁷]dec-2-yl-2-pyrrolidinone;
3-[(2-fluoro-3-methylphenyl)methyl]-3-methyl-1-tricyclo[3.3.1.1³,⁷]dec-2-yl-2-pyrrolidinone;
3-[(3-methoxyphenyl)methyl]-3-methyl-1-tricyclo[3.3.1.1³,⁷]dec-2-yl-2-pyrrolidinone;
3-[(3,5-dimethylphenyl)methyl]-3-methyl-1-tricyclo[3.3.1.1³,⁷]dec-2-yl-2-pyrrolidinone;
3-[(3-methoxyphenyl)methyl]-1-tricyclo[3.3.1.1³,⁷]dec-2-yl-2-piperidinone;
3-[(2-fluoro-3-methylphenyl)methyl]-1-tricyclo[3.3.1.1³,⁷]dec-2-yl-2-piperidinone;
3-[(4-fluorophenyl)methyl]-3-methyl-1-tricyclo[3.3.1.1³,⁷]dec-2-yl-2-pyrrolidinone;
3-Benzyl-1-(5-hydroxy-tricyclo[3.3.1.13,7]dec-2-yl)-pyrrolidin-2-one;
3-Benzyl-1-(5-hydroxy-tricyclo[3.3.1.13,7]dec-2-yl)-3-methyl-pyrrolidin-2-one;
3-(2-Fluoro-3-methyl-benzyl)-1-(5-hydroxy-tricyclo[3.3.1.13,7]dec-2-yl)pyrrolidin-2-one;
3-(2-Fluoro-3-methyl-benzyl)-1'-(5-hydroxy-tricyclo[3.3.1.13,7]dec-2-yl)-3-methyl-pyrrolidin-2-one;

the N-oxides, pharmaceutically acceptable addition salts or a stereochemically isomeric forms thereof.

In a more preferred embodiment the compounds of formula (I) are selected from the group consisting of;

3-[(3,5-dimethoxyphenyl)methyl]-1-tricyclo[3.3.1.1³,⁷]dec-2-yl-2-pyrrolidinone;
3-[(4-methylphenyl)methyl]-1-tricyclo[3.3.1.1³,⁷]dec-2-yl-2-pyrrolidinone;
3-[(2-fluoro-3-methylphenyl)methyl]-3-methyl-1-tricyclo[3.3.1.1³,⁷]dec-2-yl-2-pyrrolidinone;
3-[(3-methoxyphenyl)methyl]-3-methyl-1-tricyclo[3.3.1.1³,⁷]dec-2-yl-2-pyrrolidinone;
3-Benzyl-1-(5-hydroxy-tricyclo[3.3.1.13,7]dec-2-yl)-pyrrolidin-2-one;
3-Benzyl-1-(5-hydroxy-tricyclo[3.3.1.13,7]dec-2-yl)-3-methyl-pyrrolidin-2-one;
3-(2-Fluoro-3-methyl-benzyl)-1-(5-hydroxy-tricyclo[3.3.1.13,7]dec-2-yl)pyrrolidin-2-one;
3-(2-Fluoro-3-methyl-benzyl)-1-(5-hydroxy-tricyclo[3.3.1.13,7]dec-2-yl)-3-methyl-pyrrolidin-2-one;

the N-oxides, pharmaceutically acceptable addition salts or a stereochemically isomeric forms thereof.

According to a further aspect, the present invention provides the compounds of formula

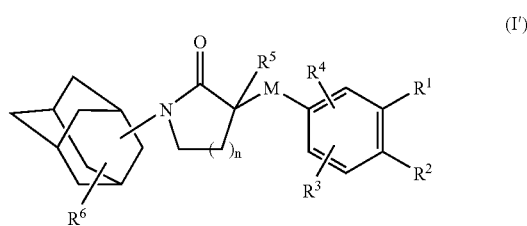

(I')

the N-oxide forms, the pharmaceutically acceptable addition salts and the stereochemically isomeric forms thereof, wherein n is 1 or 2;
M represents a direct bond or a $C_{1-3}$alkyl linker optionally substituted with one or two substituents selected from $C_{1-4}$alkyl, $C_{1-3}$alkyloxy-$C_{1-4}$alkyl-, hydroxy-$C_{1-4}$alkyl-, hydroxy, $C_{1-3}$alkyloxy- or phenyl-$C_{1-4}$alkyl-;
R¹ and R² each independently represent hydrogen, halo, cyano, hydroxy, $C_{1-4}$alkyl optionally substituted with halo,
$C_{1-4}$alkyloxy-optionally substituted with one or where possible two or three substituents selected from hydroxy, Ar¹ and halo;
R³ represents hydrogen, halo, $C_{1-4}$alkyl, $C_{1-4}$alkyloxy-, cyano or hydroxy;
R⁴ represents hydrogen, halo, $C_{1-4}$alkyl, hydroxy, cyano or $C_{1-4}$alkyloxy-optionally substituted with one or where possible two or three substituents selected from hydroxy and halo;
R⁵ represents hydrogen, $C_{1-4}$alkyl or Ar²—$C_{1-4}$alkyl-;
R⁶ represents hydrogen, hydroxy, halo, $C_{1-4}$alkyl or $C_{1-4}$alkyloxy-;
Ar¹ and Ar² each independently represent phenyl or naphtyl wherein said phenyl and naphtyl are optionally substituted with $C_{1-4}$alkyl, $C_{1-4}$alkyloxy-, or phenyl-$C_{1-4}$alkyl.

Another group of interesting compounds consists of those compounds of formula (I') wherein one or more of the following restrictions apply:

i. n is 1 or 2;
ii. M represents a $C_1$-linker;
iii. R¹ and R² represent hydrogen, $C_{1-4}$alkyl or $C_{1-4}$alkyloxy, in particular methyl or methoxy;
iv. R³ represents hydrogen or $C_{1-4}$alkyloxy, in particular hydrogen or methoxy;
v. R⁴ represents hydrogen or halo;
vi. R⁵ represents hydrogen or $C_{1-4}$alkyl, in particular hydrogen or methyl;
vii. R⁶ represents hydrogen or hydroxy.

Also of interest are those compounds of formula (I') wherein one or more of the following restrictions apply:

i. n is 1 or 2;
ii. M represents a $C_1$-linker;
iii. R¹ represents hydrogen, $C_{1-4}$alkyl or $C_{1-4}$alkyloxy, in particular methyl or methoxy;
iv. R² represents hydrogen, $C_{1-4}$alkyl or $C_{1-4}$alkyloxy, in particular hydrogen;
v. R³ represents hydrogen or $C_{1-4}$alkyloxy, in particular hydrogen or methoxy;
vi. R⁴ represents hydrogen or halo;
vii. R⁵ represents hydrogen or $C_{1-4}$alkyl, in particular hydrogen or methyl;
viii. R⁶ represents hydrogen or hydroxy.

Other special group of compounds are:
those compounds of formula (I) wherein n is 1.
those compounds of formula (I) wherein the adamantly substituent is attached at position 2 to the remainder of the molecule.
those compounds of formula (I) wherein R¹ or R² represents hydrogen.
those compounds of formula (I) wherein R³ is at the meta-position with respect to M.
those compounds of formula (I) wherein the R⁶ substituent is at position 4 vis-à-vis the attachment point of the adamantyl to the remainder of the molecule.

In a further aspect the present invention provides any of the aforementioned group of compounds for use as a medicine. In particular in the treatment or prevention of pathologies associated with excess cortisol formation such as obesity, diabetes, obesity related cardiovascular diseases and glaucoma.

The 1,3-pyrrolidinine derivatives of the present invention are generally prepared by alkylation of the appropriate lactam (II) with an appropriate alkyl halide (III) in the presence of a base such as for example (diisopropylamino)lithium (LDA) or sec-butyllithium, optionally in the present of a co-solvent such as for example N,N',N''-Hexamethylphosphoramide (HMPA) or a salt such as for example LiBr (Scheme 1). This reaction is usually performed in an inert solvent such as for example diisopropylether, tetrahydrofuran or methylene chloride. The reaction temperature and the reaction time may be altered depending on the starting material or reagents but is usually performed within a couple of hours at low temperatures (−50° C.–−90° C.). In some cases the coupling reaction is slow and the mixture has to be kept until completion. In these cases the temperature could be enhanced up to (−10° C.–−30° C.).

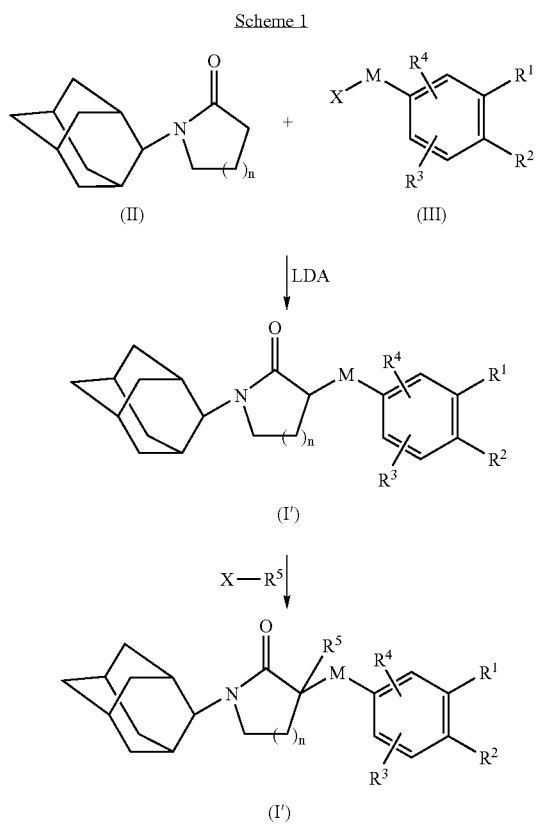

The appropriate lactam of formula (II) hereinbefore, is generally prepared by reacting adamantan-2-one (IV) with the appropriate aminoalkylic acid in the presence of an acid, such as for example formic acid (Scheme 2). The reaction is typically performed at an elevated temperature, for example in a range from 100-200° C., till no more adamantanone can be detected. Upon completion of the reaction, the reaction mixture is cooled, alkalized using for example sodiumcarbonate and extracted with ether to provide the lactam of formula (II).

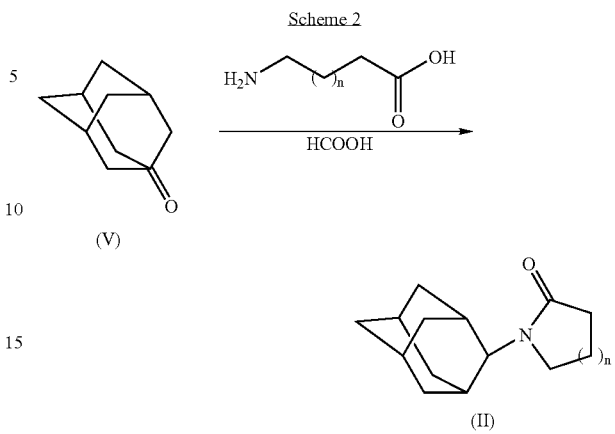

Further examples for the synthesis of compounds of formula (I) using anyone of the above-mentioned synthesis methods, are provided in the experimental part hereinafter.

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer;

It will be appreciated by those skilled in the art that in the processes described above the functional groups of intermediate compounds may need to be blocked by protecting groups.

Functional groups which it is desirable to protect include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$ alkyl or benzyl esters.

The protection and deprotection of functional groups may take place before or after a reaction step.

The use of protecting groups is fully described in 'Protective Groups in Organic Synthesis' $2^{nd}$ edition, T W Greene & P G M Wutz, Wiley Interscience (1991).

Additionally, the N-atoms in compounds of formula (I) can be methylated by art-known methods using $CH_3$—I in a suitable solvent such as, for example 2-propanone, tetrahydrofuran or dimethylformamide.

The compounds of formula (I), can also be converted into each other following art-known procedures of functional group transformation of which some examples are mentioned hereinabove.

The compounds of formula (I), may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I), may be obtained by the application of art-known procedures. Diastereomers may be separated by physical methods such as selective crystallization and chromatographic techniques, e.g. counter-current distribution, liquid chromatography and the like.

Some of the compounds of formula (I), and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures.

The compounds of the present invention are useful because they possess pharmacological properties. They can therefore be used as medicines, in particular to treat pathologies associated with excess cortisol formation such as for example, obesity, diabetes, obesity related cardiovascular diseases, and glaucoma.

As described in the experimental part hereinafter, the inhibitory effect of the present compounds on the 11β-HSD1-reductase activity (conversion of cortison into cortisol) has been demonstrated in vitro, in an enzymatic assay using the recombinant 11β-HSD1 enzyme, by measuring the conversion of cortison into cortisol using HPLC purification and quantification methods. 11β-HSD1-reductase inhibition was also demonstrated in vitro, in a cell based assay comprising contacting the cells, expressing 11β-HSD1 with the compounds to be tested and assessing the effect of said compounds on the formation of cortisol in the cellular medium of these cells. The cells preferably used in an assay of the present invention are selected from the group consisting of mouse fibroblast 3T3-L1 cells, HepG2 cells, pig kidney cell, in particular LCC-PK1 cells and rat hepatocytes.

Accordingly, the present invention provides the compounds of formula (I) and their pharmaceutically acceptable N-oxides, addition salts, quaternary amines and stereochemically isomeric forms for use in therapy. More particular in the treatment or prevention of pathologies associated with excess cortisol formation such as obesity, diabetes, obesity related cardiovascular diseases and glaucoma. The compounds of formula (I) and their pharmaceutically acceptable N-oxides, addition salts, quaternary amines and the stereochemically isomeric forms may hereinafter be referred to as compounds according to the invention.

In view of the utility of the compounds according to the invention, there is provided a method for the treatment of an animal, for example, a mammal including humans, suffering from a pathology associated with excess cortisol formation, which comprises administering an effective amount of a compound according to the present invention. Said method comprising the systemic or topical administration of an effective amount of a compound according to the invention, to warm-blooded animals, including humans.

It is thus an object of the present invention to provide a compound according to the present invention for use as a medicine. In particular to use the compound according to the present invention in the manufacture of a medicament for treating pathologies associated with excess cortisol formation such as for example, obesity, diabetes, obesity related cardiovascular diseases, and glaucoma.

The amount of a compound according to the present invention, also referred to here as the active ingredient, which is required to achieve a therapeutical effect will be, of course, vary with the particular compound, the route of administration, the age and condition of the recipient, and the particular disorder or disease being treated. A suitable daily dose would be from 0.001 mg/kg to 500 mg/kg body weight, in particular from 0.005 mg/kg to 100 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous, or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment. As appropriate compositions for topical application there may be cited all compositions usually employed for topically administering drugs e.g. creams, gellies, dressings, shampoos, tinctures, pastes, ointments, salves, powders and the like. Application of said compositions may be by aerosol, e.g. with a propellant such as nitrogen, carbon dioxide, a freon, or without a propellant such as a pump spray, drops, lotions, or a semisolid such as a thickened composition which can be applied by a swab. In particular, semisolid compositions such as salves, creams, gellies, ointments and the like will conveniently be used.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In order to enhance the solubility and/or the stability of the compounds of formula (I) in pharmaceutical compositions, it can be advantageous to employ α-, β- or γ-cyclodextrins or their derivatives. Also co-solvents such as alcohols may improve the solubility and/or the stability of the compounds of formula (I) in pharmaceutical compositions. In the preparation of aqueous compositions, addition salts of the subject compounds are obviously more suitable due to their increased water solubility.

EXPERIMENTAL PART

Hereinafter, the term 'DCM means dichloromethane, "DIPE" is defined as diisopropyl ether, "DMF" is defined as N,N-dimethylformamide, 'Et$_2$O' means diethylether, "EtOAc" is defined as ethyl acetate, 'LDA' means (diisopropylamino)lithium, 'THF' means tetrahydrofuran.

A. Preparation of the Intermediates

Example A1

Preparation of

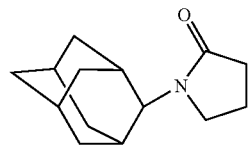

Intermediate 1

In a round bottom flask were placed adamantan-2-one (5.00 g, 33.28 mmol), γ-aminobutyric acid (6.86 g, 66.56 mmol) and 8.3 ml formic acid. The mixture was a heated at 140-160° C. for 17 hours until no more adamantanone could be monitored. TLC of intermediate 1: R$_f$=0.24 in Et$_2$O+1 drop CH$_3$COOH, eluted 2 times. The mixture was poured on crushed ice, then it was alkalized (NaHCO$_3$), extracted with Et$_2$O (3×70 ml) and dried (MgSO$_4$). After evaporation of the solvent 4.95 g of crude intermediate 1 were obtained. For purification it was chromatographed (column h=279 mm, Ø=46 mm, 170 g silica gel 230-400 mesh, eluent Et$_2$O) to give 4.36 g (59%) of pure intermediate 1 (colourless crystals).

Example A2 a) Preparation of

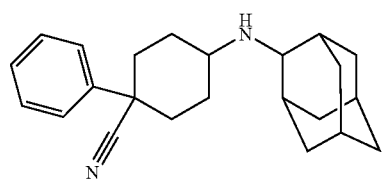

Intermediate 2

A mixture of 4-oxo-1-phenyl-cyclohexanecarbonitrile (0.025 mol), tricyclo[3.3.1.13,7]decan-2-amine, hydrochloride (0.025 mol) and acetic acid, potassium salt (5 g) in methanol (150 ml) was hydrogenated overnight at 50° C. with palladium on activated carbon (10%) (2 g) as a catalyst in the presence of a thiophene solution (1 ml). After uptake of hydrogen (1 equiv.), the catalyst was filtered off and the filtrate was evaporated. The residue was dissolved in DCM and washed with water. The organic layer was separated, dried, filtered and the solvent was evaporated, yielding 8 g of intermediate 2.

b) Preparation of

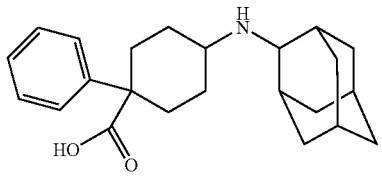

Intermediate 3

A mixture of intermediate 2 (0.0029 mol) and potassium hydroxide (0.0145 mol) in 1,2-ethanediol (15 ml) was stirred and refluxed over the weekend. The reaction mixture was cooled, poured out into water and extracted with DCM. The aqueous layer was acidified with citric acid (pH: 5) and extracted with DCM. The organic layer was separated, dried, filtered and the solvent was evaporated, yielding 1.8 g of intermediate 3.

Example A3 a) Preparation of

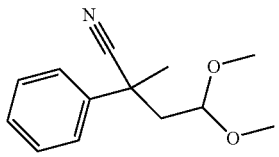

Intermediate 4

Sodium hydride (0.08 mol) was added under $N_2$ flow to a mixture of α-methyl-benzeneacetonitrile (0.076 mol) in DMF (100-ml). The mixture was stirred for 2.5 hours, then 2-bromo-1,1-dimethoxy-ethane (0.1 mol) was added dropwise and the reaction mixture was stirred for 3 hours. The mixture was poured out into ice and extracted with DCM. The organic layer was separated, washed, dried, filtered and the solvent was evaporated, yielding 15 g (90%) of intermediate 4.

b) Preparation of

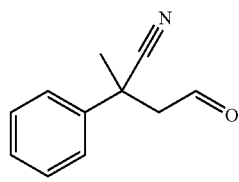

Intermediate 5

A mixture of intermediate 4 (0.022 mol) in formic acid (25 ml) was stirred for 10 minutes at 50° C. and was then cooled. The reaction mixture was poured out into ice and was extracted with DIPE. The organic layer was separated, washed with a $Na_2CO_3$ solution and with water, then dried ($MgSO_4$), filtered off and the solvent was evaporated, yielding 3 g (79%) of intermediate 5.

c) Preparation of

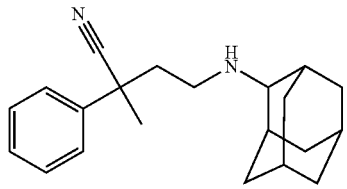

Intermediate 6

A mixture of intermediate 5 (0.017 mol), tricyclo[3.3.1.1³,⁷]decan-2-amine, hydrochloride (0.017 mol) and acetic acid, potassium salt (3 g) in methanol (50 ml) was hydrogenated overnight with palladium on the activated carbon (0.5 g) as a catalyst in the presence of a thiophene solution (0.5 ml). After uptake of hydrogen (1 equiv.), the catalyst was filtered off and the filtrate was evaporated. The obtained residue was stirred in DIPE, filtered and the filtrate was evaporated, yielding 3.7 g (71%) of intermediate 6.

d) Preparation of

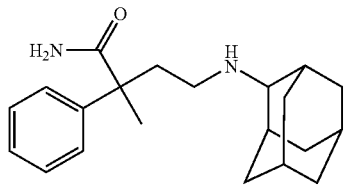

Intermediate 7

A mixture of intermediate 6 (0.0094 mol) in sulfuric acid (25 ml) was stirred overnight at room temperature and the reaction mixture was poured out into ice, then the mixture was neutralised with a NaOH solution and extracted with EtOAc. The organic layer was separated, washed, dried, filtered off and the solvent was evaporated, yielding 3.7 g of intermediate 7.

e) Preparation of

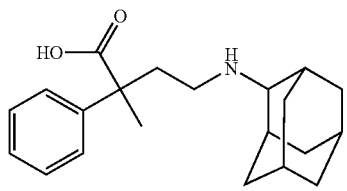

Intermediate 8

A mixture of intermediate 7 (0.01 mol) in hydrobromic acid (48%) (50 ml) was stirred and refluxed for 2 hours, then the reaction mixture was cooled and filtered. The filter residue was washed with water and dried, yielding 2.3 g (57%) of intermediate 8.

Example A4 a) Preparation of

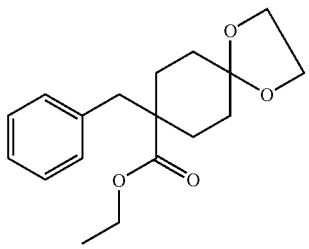

Intermediate 9

A mixture of N-(1-methylethyl)-2-propanamine (0.016 mol) in THF (15 ml) was stirred under $N_2$ on ice with methanol (−15° C.), then a solution of n-butyllithium 2.5M in hexane (0.016 mol) was added dropwise (−10° C.) and the resulting mixture was stirred for 10 minutes. A mixture of 1,4-dioxaspiro[4,5]decane-8-carboxylic acid, ethyl ester (0.016 mol) in THF (15 ml) was added dropwise at −10° C. and the mixture was stirred for 30 minutes, then a mixture of (bromomethyl)benzene (0.016 mol) in THF (15 ml) was added dropwise at −10° C. The reaction mixture was stirred for 1 hour and was then stirred overnight at room temperature. The mixture was poured out into a saturated $NH_4Cl$ solution and extracted with DIPE. The organic layer was separated, washed, dried, filtered off and the solvent was evaporated. The residue was purified by flash column chromatography. The product fractions were collected and the solvent was evaporated, yielding 2.2 g (46%) of intermediate 9.

b) Preparation of

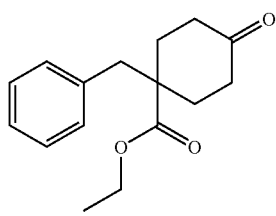

Intermediate 10

A mixture of intermediate 9 (0.0072 mol) in 2-propanone (50 ml) and hydrochloric acid (2.5N) (50 ml) was stirred overnight and then the reaction mixture was poured out into DCM. The organic layer was separated, washed, dried, filtered off and the solvent was evaporated, yielding 1.9 g of intermediate 10.

c) Preparation of

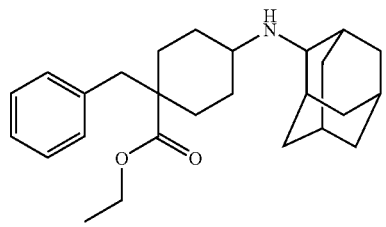

Intermediate 11

A mixture of intermediate 10 (0.0073 mol), tricyclo[3.3.1.1<sup>3,7</sup>]decan-2-amine, hydrochloride (0.009 mol) and acetic acid, potassium salt (1 g) in ethanol (50 ml) was hydrogenated overnight at 50° C. with palladium on activated carbon (0.5 g) as a catalyst in the presence of a thiophene solution (0.5 ml). After uptake of hydrogen (1 equiv.), the catalyst was filtered off and the filtrate was evaporated, yielding 2.9 g of intermediate 11.

d) Preparation of

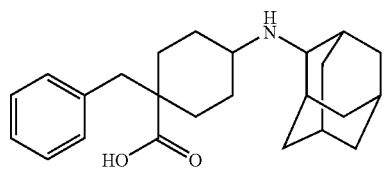

Intermediate 12

A mixture of intermediate 11 (0.0043 mol) and potassium hydroxide (5 g) in ethanol (80 ml) and water (20 ml) was stirred and refluxed for 1 week and then the solvent was evaporated. The residue was dissolved in water and washed with DCM. The aqueous layer was acidified with HCl and extracted with DCM. The organic layer was separated, dried, filtered off and the solvent was evaporated, yielding 0.774 g of intermediate 12.

Example A5 a) Preparation

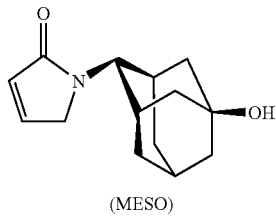

(MESO)

Intermediate 13

A mixture of 2,5-dihydro-2,5-dimethoxy-furan (0.01 mol) and 4-amino-, (1α,3α,4α,5β,7α)-tricyclo[3.3.1.1<sup>3,7</sup>]decan1-ol (0.01 mol) in water (50 ml) was stirred at room temperature. Hydrochloric acid concentrated (2 ml) was added and the reaction mixture was stirred overnight. The acidic mixture - was neutralized with an aqueous NaHCO$_3$ solution. This mixture was extracted with DCM (3×). The combined organic layers were dried, filtered and the solvent evaporated, yielding 1.5 g of intermediate 13.

b) Preparation of

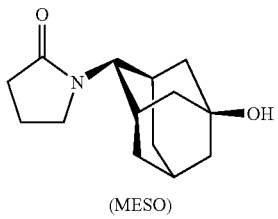

(MESO)

Intermediate 14

A mixture of intermediate 13 (0.0064 mol) in methanol (150 ml) was stirred and hydrogenated overnight with palladium on activated carbon 10% (0.5 g) as a catalyst. After uptake of hydrogen (1 equiv), the catalyst was filtered off and the filtrate was evaporated, yielding 1.2 g of intermediate 14.

B. Preparation of the Compounds

Example B1

Preparation of

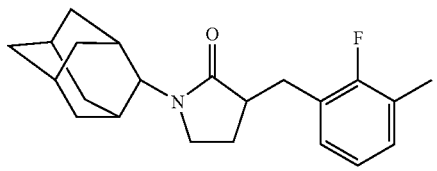

Compound 1

In a flame dried Schlenk-flask 0.20 g (0.92 mmol) of intermediate 1 in 10 ml THF were cooled to −80° C. LDA (1.3 equivalent, 0.59 ml, ca. 2M commercial solution in THF/heptane/ethylbenzene) was introduced via syringe and the mixture was stirred for 30 min at −80° C. 2-Fluoro-3-methylbenzyl bromide (0.19 g, 0.96 mmol) was introduced and the reaction mixture was stirred for 1 h at −80° C. The temperature was raised slowly to −50° C. and kept for 4 hours. The mixture was quenched with 2N HCl, then extracted with Et$_2$O and the organic layer washed with NaHCO$_3$ (5% aq.), H$_2$O, and dried with Na$_2$SO$_4$. After evaporation of the solvent the crude product was chromatographed (column h=380 mm, Ø=17 mm, 30 g silicagel 230-400 mesh, eluent petroleum ether/Et$_2$O=1:1) to give 0.22 g (71%) of compound 1 (colourless crystals).

Example B2

Preparation of

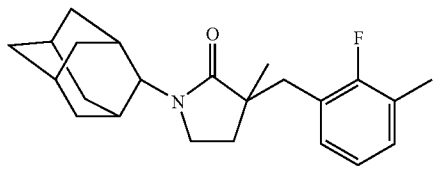

Compound 2

In a flame dried Schlenk-flask 0.16 g (0.47 mmol) of compound 1 in 10 ml THF were cooled to −80° C. LDA (1.3 equivalent, 0.31 ml, ca. 2M commercial solution in THF/heptane/ethylbenzene) was introduced via syringe and the mixture was stirred for 1 hour at −80° C. Methyl iodide (0.09 g, 0.66 mmol) was introduced and the reaction mixture was stirred for 3 hours at −80° C. It was kept over the night at −20° C. The mixture was quenched with 2N HCl, then extracted with Et$_2$O and the organic layer washed with NaHCO$_3$ (5% aq.), H$_2$O, and dried with Na$_2$SO$_4$. After evaporation of the solvent the crude product was chromatographed (column h=460 mm, Ø=13 mm, 10 g silicagel 230-400 mesh, eluent petroleum ether/Et$_2$O=1:1) to give 0.90 g (53%) of compound 2, 0.012 g mixed fraction and 0.016 g by-product. (Comment: could be better without keeping the reaction mixture overnight at −20° C.).

Table 1 lists the compounds that were prepared according to the above Examples.

TABLE 1

| Co. No. 3 | Co. No. 18 |
|---|---|
| 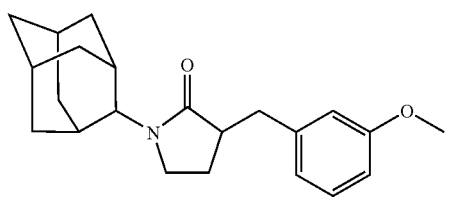 | 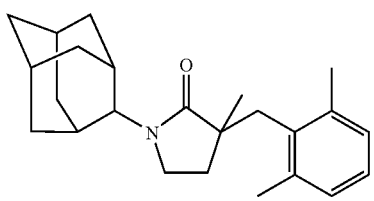 |

TABLE 1-continued
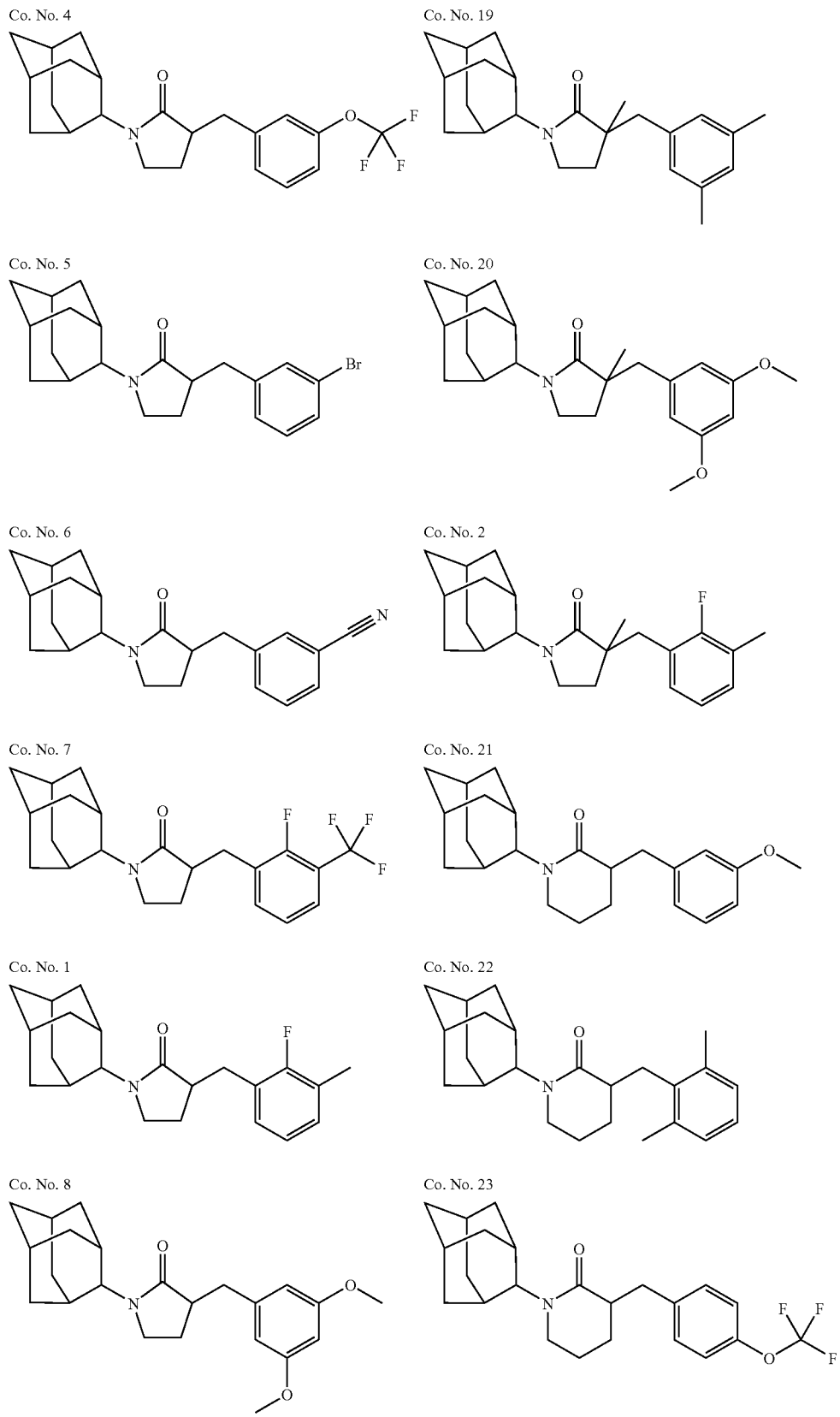

TABLE 1-continued
Co. No. 9
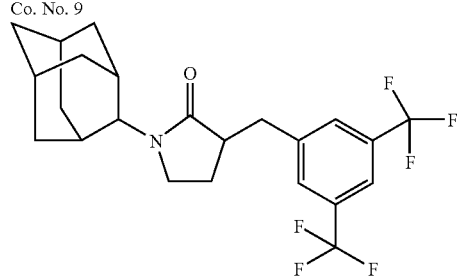
Co. No. 24
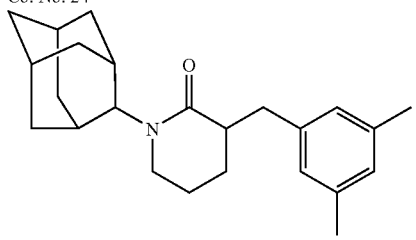
Co. No. 10
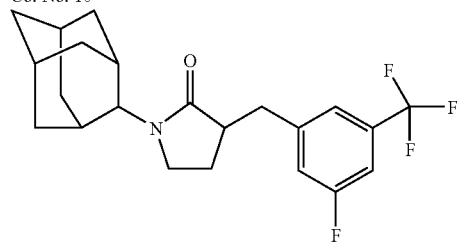
Co. No. 25
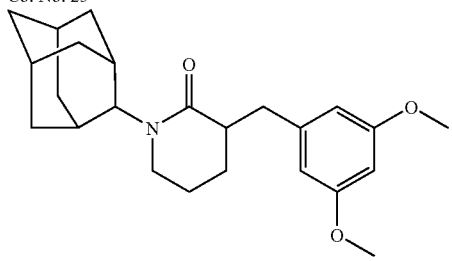
Co. No. 11
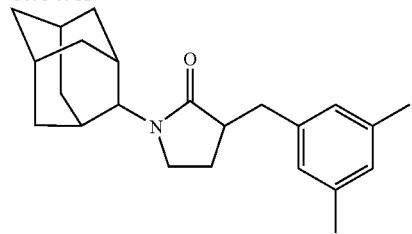
Co. No. 26
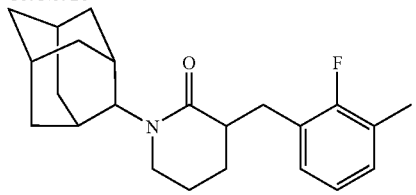
Co. No. 12
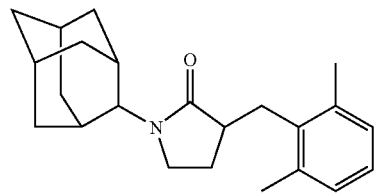
Co. No. 27
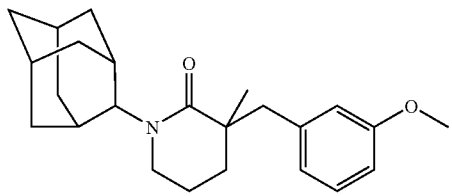
Co. No. 13
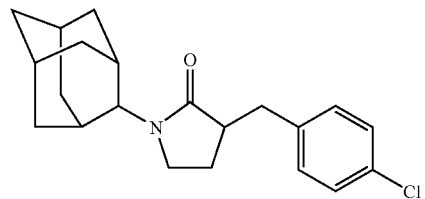
Co. No. 28
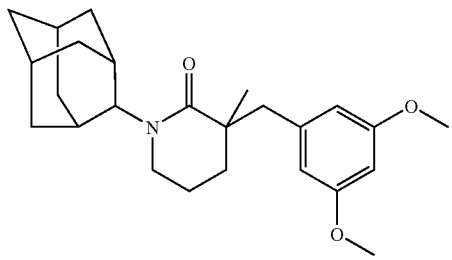
Co. No. 14
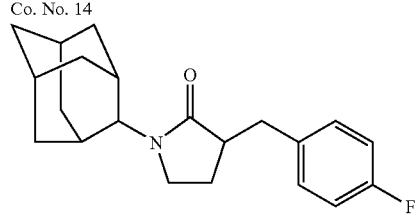
Co. No. 29
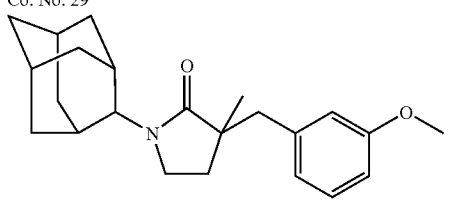

TABLE 1-continued

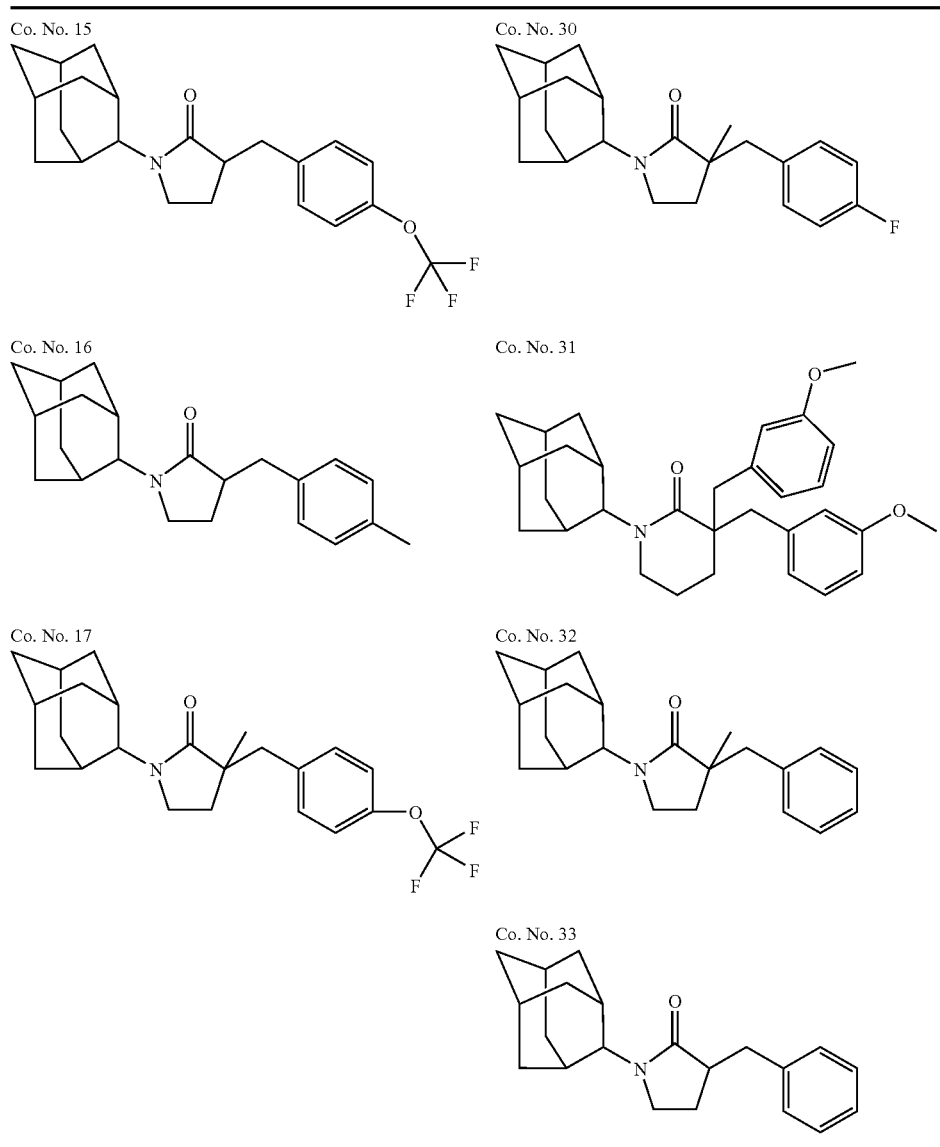

| Co. No. | NMR data | melting point (° C.) |
|---|---|---|
| 3 | CDCl$_3$; 1.55-2.23(m, 14H-adamantane, H$^A$—CH$_2$, H$^B$—CH$_2$); 2.57-2.77(m, CH, H$^A$—CH$_2$); 2.99-3.21(m, H$^B$—CH$_2$); 3.39-3.48(m, CH$_2$); 3.77(s, CH$_3$); 3.98(t, CH); 6.68-6.81(m, 3H-aromatic); 7.12-7.22(m, 1H-aromatic) | |
| 4 | CDCl$_3$; 1.58-2.22(m, 14H-adamantane, H$^A$—CH$_2$, H$^B$—CH$_2$); 2.62-2.78(m, CH, H$^A$—CH$_2$); 3.13-3.27(m, H$^B$—CH$_2$); 3.41-3.52(m, CH$_2$); 3.99(t, CH); 7.02-7.10(m, 2H-aromatic); 7.12-7.19(m, 1H-aromatic); 7.25-7.36(m, 1H-aromatic) | 58-59.5 |
| 5 | CDCl$_3$; 1.56-2.22(m, 14H-adamantane, H$^A$—CH$_2$, H$^B$—CH$_2$); 2.59-2.74(m, CH, H$^A$—CH$_2$); 3.05-3.20(m, H$^B$—CH$_2$); 3.38-3.50(m, CH$_2$); 3.97(t, CH); 7.11(m, 2H-aromatic); 7.27-7.37(m, 2H-aromatic) | 83.5-85.0 |
| 6 | CDCl$_3$; 1.53-2.22(m, 14H-adamantane, H$^A$—CH$_2$, H$^B$—CH$_2$); 2.59-2.81(m, CH, H$^A$—CH$_2$); 3.04-3.21(m, H$^B$—CH$_2$); 3.38-3.48(m, CH$_2$); 3.95(t, CH); 7.30-7.51(m, 4H-aromatic) | 110.5-111.5 |
| 7 | CDCl$_3$; 1.55-2.22(m, 14H-adamantane, H$^A$—CH$_2$, H$^B$—CH$_2$); 2.68-2.87(m, CH, H$^A$—CH$_2$); 3.16-3.31(m, H$^B$—CH$_2$); 3.40-3.59(m, CH$_2$); 3.98(t, CH); 7.08-7.18(t, 1H-aromatic), 7.39-7.55(m, 2H-aromatic) | 103.5-105 |
| 1 | CDCl$_3$; 1.57-2.22(m, 14H-adamantane, H$^A$—CH$_2$, H$^B$—CH$_2$); 2.25(d, CH$_3$); 2.58-2.68(m, CH, H$^A$—CH$_2$); 3.13-3.29(m, H$^B$—CH$_2$); 3.48-3.57(m, CH$_2$); 3.99(t, CH); 6.68-7.09(m, 3H-aromatic) | 101-102 |

-continued

| Co. No. | NMR data | melting point (° C.) |
|---|---|---|
| 8 | CDCl$_3$; 1.49-2.16(m, 14H-adamantane, H$^A$—CH$_2$, H$^B$—CH$_2$); 2.42-2.67(m, CH, H$^A$—CH$_2$); 3.00-3.09(dd, H$^B$—CH$_2$); 3.32-3.42(m, CH$_2$); 3.68(s, 2x CH$_3$); 3.91(t, CH); 6.21-6.32(m, 3H-aromatic) | |
| 9 | CDCl$_3$; 1.53-2.23(m, 14H-adamantane, H$^A$—CH$_2$, H$^B$—CH$_2$); 2.67-2.80(m, CH); 2.80-2.92(m, H$^A$—CH$_2$); 3.20-3.32(dd, H$^B$—CH$_2$); 3.42-3.57(m, CH$_2$); 3.97(t, CH); 7.61-7.73(m, 3H-aromatic) | |
| 10 | CDCl$_3$; 1.57-2.23(m, 14H-adamantane, H$^A$—CH$_2$, H$^B$—CH$_2$); 2.69-2.86(m, CH, H$^A$—CH$_2$); 3.13-3.29(m, H$^B$—CH$_2$); 3.42-3.54(m, CH$_2$); 3.98(t, CH); 7.09-7.20(m, 2H-aromatic); 7.26(s, 1H-aromatic) | 84-85 |
| 11 | CDCl$_3$; 1.57-2.23(m, 14H-adamantane, H$^A$—CH$_2$, H$^B$—CH$_2$); 2.27(s, 2x CH$_3$); 2.51-2.73(m, CH, H$^A$—CH$_2$); 3.10(dd, H$^B$—CH$_2$); 3.37-3.48(m, CH$_2$); 3.99(t, CH); 6.83(m, 3H-aromatic) | 85.5-87.0 |
| 12 | CDCl$_3$; 1.62-2.32(m, 14H-adamantane, H$^A$—CH$_2$, H$^B$—CH$_2$); 2.37(s, 2x CH$_3$); 2.50-2.75(m, CH, H$^A$—CH$_2$); 3.28-3.50(m, H$^A$—CH$_2$, CH$_2$); 3.59-3.71(m, H$^B$—CH$_2$); 4.02(t, CH); 7.01(s, 3H-aromatic) | 99-101 |
| 13 | CDCl$_3$; 1.49-2.15(m, 14H-adamantane, H$^A$—CH$_2$, H$^B$—CH$_2$); 2.54-2.69(m, CH, H$^A$—CH$_2$); 2.98-3.11(m, H$^B$—CH$_2$); 3.32-3.42(m, CH$_2$); 3.91(t, CH); 7.02-7.21(m, 4H-aromatic) | 135.5-136.5 |
| 14 | CDCl$_3$; 1.55-2.20(m, 14H-adamantane, H$^A$—CH$_2$, H$^B$—CH$_2$); 2.57-2.72(m, CH, H$^A$—CH$_2$); 3.01-3.17(m, H$^B$—CH$_2$); 3.35-3.50(m, CH$_2$); 3.96(t, CH); 6.88-6.99(m, 2H-aromatic); 7.10-7.20(m, 2H-aromatic) | 105-106 |
| 15 | CDCl$_3$; 1.52-2.21(m, 14H-adamantane, H$^A$—CH$_2$, H$^B$—CH$_2$); 2.49-2.26(m, CH, H$^A$—CH$_2$); 3.03-3.19(m, H$^B$—CH$_2$); 3.34-3.49(m, CH$_2$); 3.96(t, CH); 7.03-7.13(m, 2H-aromatic); 7.16-7.25(m, 2H-aromatic) | |
| 16 | CDCl$_3$; 1.57-2.23(m, 14H-adamantane, H$^A$—CH$_2$, H$^B$—CH$_2$); 2.31(s, CH$_3$); 2.55-2.72(m, CH, H$^A$—CH$_2$); 3.18-3.22(m, H$^B$—CH$_2$); 3.40-3.48(m, CH$_2$); 3.99(t, CH); 7.08(m, 4H-aromatic) | 109-110.5 |
| 17 | CDCl$_3$; 1.20(s, CH$_3$)1.50-2.16(m, 14H-adamantane, H$^A$—CH$_2$, H$^B$—CH$_2$); 2.59(d, H$^A$—CH$_2$); 2.88-3.00(m, H$^A$—CH$_2$); 3.00(d, H$^B$—CH$_2$); 3.32-3.45(m, H$^B$—CH$_2$); 3.92(t, CH); 7.08(d, 2H-aromatic); 7.22(d, 2H-aromatic) | 100.5-101.5 |
| 18 | CDCl$_3$; 1.20(s, CH$_3$); 1.53-2.22(m, 14H-adamantane, H$^A$—CH$_2$, H$^B$—CH$_2$); 2.29(s, 2x CH$_3$); 2.85(d, H$^A$—CH$_2$); 3.12-3.23(m, H$^A$—CH$_2$); 3.26(d, H$^B$—CH$_2$); 3.33-3.50(m, H$^B$—CH$_2$); 3.95(t, CH); 6.99(s, 3H-aromatic) | |
| 19 | CDCl$_3$; 1.18(s, CH$_3$); 1.46-2.17(m, 14H-adamantane, H$^A$—CH$_2$, H$^B$—CH$_2$); 2.24(s, 2x CH$_3$); 2.47(d, H$^A$—CH$_2$); 2.78-2.88(m, H$^A$—CH$_2$); 2.90(d, H$^B$—CH$_2$); 3.27-3.38(m, H$^B$—CH$_2$); 3.92(t, CH); 6.73-6.83(m, 3H-aromatic) | 85-87 |
| 20 | CDCl$_3$; 1.15(s, CH$_3$); 1.42-2.23(m, 14H-adamantane, H$^A$—CH$_2$, H$^B$—CH$_2$); 2.46(d, H$^A$—CH$_2$); 2.88(d, H$^B$—CH$_2$); 2.86-2.97(m, H$^A$—CH$_2$); 3.27-3.39(m, H$^B$—CH$_2$); 3.70(s, 2x CH$_3$); 3.88(t, CH); 6.24-6.31(m, 3H-aromatic) | |
| 2 | CDCl$_3$; 1.16(s, CH$_3$); 1.47-2.18(m, 14H-adamantane, H$^A$—CH$_2$, H$^B$—CH$_2$); 2.23(s, CH$_3$); 2.81(d, CH$_2$); 3.05-3.18(m, H$^A$—CH$_2$); 3.34-3.47(m, H$^B$—CH$_2$); 3.93(t, CH); 6.83-7.06(m, 3H-aromatic) | 120.5-122.0 |
| 21 | CDCl$_3$; 1.31-2.23(m, 14H-adamantane, 2x CH$_2$); 2.51-2.73(m, CH, H$^A$—CH$_2$); 3.28-3.40(m, H$^B$—CH$_2$); 3.40-3.59(m, CH$_2$); 3.77(s, CH$_3$); 4.37(t, CH); 6.19-6.81(m, 3H-aromatic); 7.12-7.21(t, 1H-aromatic) | |
| 22 | CDCl$_3$; 1.42-2.27(m, 14H-adamantane, 2x CH$_2$); 2.38(s, 2x CH$_3$); 2.43-2.59(m, CH); 2.64-2.78(m, H$^A$—CH$_2$); 3.47-3.60(m, CH$_2$, H$^B$—CH$_2$); 4.42(t, CH); 7.01(s, 3H-aromatic) | 145-149 |
| 23 | CDCl$_3$; 1.28-2.24(m, 14H-adamantane, 2x CH$_2$); 2.46-2.62(m, CH); 2.68-2.82(m, H$^A$—CH$_2$); 3.21-3.36(dd, H$^B$—CH$_2$); 3.36-3.61(m, CH$_2$); 4.35(t, CH); 7.03-7.27(m, 4H-aromatic) | |
| 24 | CDCl$_3$; 1.30-2.26(m, 14H-adamantane, 2x CH$_2$); 2.27(s, 2x CH$_3$); 2.47-2.62(m, CH); 2.60-2.72(m, H$^A$—CH$_2$); 3.29-3.31(dd, H$^B$—CH$_2$); 3.37-3.59(m, CH$_2$); 4.39(t, CH); 6.81(m, 3H-aromatic) | 116-118.5 |
| 25 | CDCl$_3$; 1.31-2.21(m, 14H-adamantane, 2x CH$_2$); 2.52-2.67(m, CH, H$^A$—CH$_2$); 3.23-3.38(m, H$^B$—CH$_2$); 3.38-3.58(m, CH$_2$); 3.74(s, 2x CH$_3$); 4.36(t, CH); 6.23-6.31(m, 1H-aromatic); 6.31-6.39(m, 2H-aromatic) | 166.5-168 |
| 26 | CDCl$_3$; 1.30-2.22(m, 14H-adamantane, 2x CH$_2$); 2.23(d, CH$_3$); 2.48-2.63(m, CH); 2.64-2.79(m, H$^A$—CH$_2$); 3.29-3.41(dd, H$^B$—CH$_2$); 3.41-3.58(m, CH$_2$); 4.34(t, CH); 6.82-7.04(m, 3H-aromatic) | 99-100 |
| 27 | CDCl$_3$; 1.24(s, CH$_3$); 1.35-2.22(m, 14H-adamantane, 2x CH$_2$); 2.51(d, H$^A$—CH$_2$); 3.19-3.30(m, H$^A$—CH$_2$, H$^B$—CH$_2$); 3.39-3.49(m, H$^B$—CH$_2$); 3.74(s, CH$_3$); 4.31(t, CH); 6.70(m, 3H-aromatic); 7.11(1H-aromatic) | 79-81.5 |
| 28 | CDCl$_3$; 1.26(s, CH$_3$); 1.48-2.22(m, 14H-adamantane, 2x CH$_2$); 2.47(d, H$^A$—CH$_2$); 3.18-3.32(m, H$^A$—CH$_2$, H$^B$—CH$_2$); 3.40-3.52(m, H$^B$—CH$_2$); 3.74(s, 2x CH$_3$); 4.33(t, CH); 6.33(m, 3H-aromatic) | |
| 29 | CDCl$_3$; 1.17(s, CH3); 1.42-2.28(m, 14H-adamantane, 2x CH$_2$); 2.54(d, H$^A$—CH$_2$); 2.84-2.95(m, H$^A$—CH$_2$); 2.93(d, H$^B$—CH$_2$); 3.28-3.40(m, H$^B$—CH$_2$); 3.75(s, CH$_3$); 3.91(t, CH); 6.19-6.30(m, 3H-aromatic); 7.09-7.18(t, 1H-aromatic) | 89.5-92.0 |

| Co. No. | NMR data | melting point (° C.) |
|---|---|---|
| 30 | CDCl$_3$; 1.16(s, CH3); 1.44-2.17(m, 14H-adamantane, CH$_2$); 2.53(d, H$^A$—CH$_2$); 2.88-3.00(m, H$^A$—CH$_2$, H$^B$—CH$_2$); 3.31-3.42(m, H$^B$—CH$_2$); 3.90(t, CH); 6.85-6.97(m, 2H-aromatic); 7.08-7.18(m, 2H-aromatic); 7.08-7.18(m, 2H-aromatic) | 162-163 |
| 31 | CDCl$_3$; 1.68-2.15(m, 14H-adamantane, 2x CH$_2$); 2.54(d, 2x H$^A$—CH$_2$); 3.08(m, CH$_2$); 3.40(d, 2x H$^B$—CH$_2$); 3.75(s, 2x CH$_3$); 4.35(t, CH); 6.68-6.79(m, 6H-aromatic); 7.08-7.18(m, 2H-aromatic) | |
| 32 | CDCl$_3$; 1.19(s, CH3); 1.49-2.14(m, 14H-adamantane, CH$_2$); 2.60(d, 1H, H$^A$—CH$_2$); 2.91(m, H$^A$—NCH$_2$); 2.98(d, 1H, H$^B$—CH$_2$); 3.37(m, H$^B$—NCH$_2$); 3.93(s, CH); 7.18-7.26(m, 5H-aromatic) | |
| 33 | CDCl$_3$; 1.57-1.94(m, 12H-adamantane, H$^A$—CH$_2$); 1.99-2.09 (m, 1H, H$^B$—CH$_2$); 2.19(brs, 2H-adamantane); 2.63-2.75(m, CH, H$^A$—CH$_2$); 3.15-3.24(m, H$^B$—CH$_2$); 3.42-3.48(m, CH$_2$); 3.99(s, CH); 7.18-7.32(m, 5H-aromatic) | |
| 34 | 1.56-2.26(m, 20H, 12H-adamantane, 4x CH$_2$); 2.30(brs, 2H-adamantane); 4.12(s, CH); 4.16(brs, CH); 7.20-7.40(m, 5H-aromatic) | |
| 35 | 1.52(s, 3H, CH3); 1.61-2.05(m, 12H-adamantane); 2.08-2.18(m, 1H, H$^A$—CH$_2$); 2.21 and 2.35(2x brs, 2H-adamantane); 2.38-2.46(m, 1H, H$^B$—CH$_2$); 3.48-3.64(m, 2H, H$^A$ and H$^B$—CH$_2$); 4.08(s, CH); 7.19-7.41(m, 5H-aromatic) | |
| 36 | 1.50-1.96(m, 20H, 12H-adamantane, 4x CH$_2$); 2.27(brs, 2H-adamantane); 2.98(s, 2H, CH$_2$); 4.04 and 4.14(2x s, 2x CH); 7.17-7.30(m, 5H-aromatic) | |
| 37 | CDCl$_3$; 1.34-1.93(m, 11H-adamantane, H$^A$—CH$_2$); 1.99-2.09(m, 1H, H$^B$—CH$_2$); 2.15(brs, 2H-adamantane); 2.42(d, 2H-adamantane); 2.63-2.75(m, CH, H$^A$—CH$_2$); 3.15-3.24(m, H$^B$—CH$_2$); 3.42-3.48(m, CH$_2$); 3.90(s, 1H-adamantane); 7.18-7.32(m, 5H-aromatic) | |
| 38 | CDCl$_3$; 1.20(s, CH$_3$); 1.34-1.93(m, 11H-adamantane, H$^A$—CH$_2$); 2.05-2.14(1H, CH$_2$); 2.27(s, 1H-adamantane); 2.37(s, 1H-adamantane); 2.60(d, 1H, CH$_2$—Ph); 2.85(m, H$^A$—NCH$_2$); 2.98(d, 1H, CH$_2$—Ph); 3.32(m, H$^B$—NCH$_2$); 3.83(s, 1H-adamantane); 7.18-7.26(m, 5H-aromatic) | |
| 39 | CDCl$_3$; 1.57-1.95(m, 11H-adamantane, H$^A$—CH$_2$); 2.05(m, H$^B$—CH$_2$); 2.17(s, 1H-adamantane); 2.25(d, CH$_3$); 2.45(d, 2H-adamantane); 2.58-2.68(m, CH, H$^A$—CH$_2$); 3.13-3.29(m, H$^B$—CH$_2$); 3.48-3.57(m, CH$_2$); 3.90(s, 1H-adamantane); 6.90-7.09(m, 3H-aromatic) | |
| 40 | CDCl$_3$; 1.20(s, CH$_3$); 1.37-2.18(m, 12H-adamantane, H$^A$—CH$_2$, H$^B$—CH$_2$); 2.25(s, CH$_3$); 2.35(d, 2H-adamantane); 2.81(d, CH$_2$); 3.05-3.18(m, H$^A$—CH$_2$); 3.34-3.47(m, H$^B$—CH$_2$); 3.87(s, 1H-adamantane); 6.85-7.06(m, 3H-aromatic) | |

Example B3

Preparation of

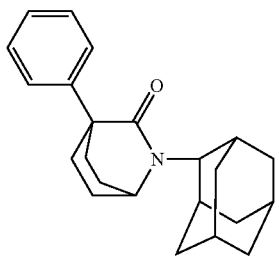

Compound 34

A mixture of intermediate (3) (0.00028 mol) and phosphorus pentachloride (0.1 g) in phosphorus oxychloride (1 ml) was stirred at 100° C. for 45 minutes, then the reaction mixture was cooled, poured out into ice, neutralised with a Na$_2$CO$_3$ soln. and extracted with DCM. The organic layer was filtered through Extrelut and the solvent was evaporated. The residue was purified by flash column chromatography on Triconex flash tubes (eluent: DCM). The product fractions were collected and the solvent was evaporated, yielding 0.051 g (54%) of compound 34.

Example B4

Preparation of

Compound 35

A mixture of intermediate 8 (0.00024 mol) in thionyl chloride (2 ml) was stirred and refluxed for 2 hours and then stirred overnight at room temperature. The solvent was evaporated and the residue was purified by flash column chromatography on Triconex flash tubes (eluent: CH$_2$Cl$_2$/EtOAc 95/5). The product fractions were collected and the solvent was evaporated, yielding, 0.0183 g (7.5%) of compound 35.

Example B5

Preparation of

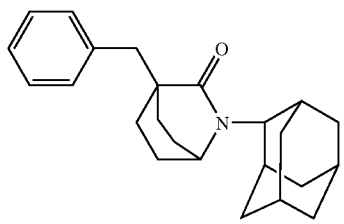

Compound 36

A mixture of intermediate 12 (0.00027 mol) and phosphorus pentachloride (0.1 g) in phosphorus oxychloride (1 ml) was stirred for 1 hour at 100° C. and after cooling the reaction mixture was poured out into ice and extracted with dichloromethane. The organic layer was washed with a $Na_2CO_3$ solution, dried, filtered off and the solvent was evaporated. The residue was purified by flash column chromatography on Triconex flash tubes (eluent: $CH_2Cl_2$/EtOAc 90/10). The product fractions were collected and the solvent was evaporated, yielding 0.027 g of compound 36.

Example B6

Preparation of

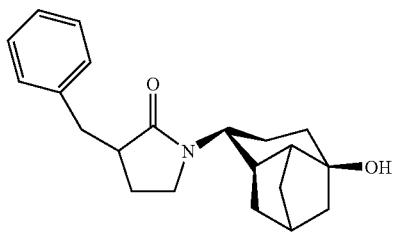

Compound 37

Reaction under $N_2$ atmosphere. A mixture of intermediate 14 (0.005 mol) in THF dry (25 ml) and 1,4-dioxane (10 ml) was stirred under ultrasonic conditions until complete dissolution. The mixture was cooled to −78° C. Sec. butyllithium 1.3M/hexane (0.013 mol) was added and the mixture was stirred for 12 hours at −30° C., then cooled to −78° C. (Bromomethyl)-benzene (0.01 mol) was added dropwise and the reaction mixture was stirred for one hour at −78° C., then stirred overnight at room temperature. The mixture was poured out into a saturated aqueous $NH_4Cl$ solution, then extracted with DCM. The separated organic layer was dried, filtered and the solvent evaporated. The residue was purified by column chromatography over silica gel (Biotage; eluent: DCM/$CH_3OH$ 99/1). The product fractions were collected and the solvent was evaporated, yielding 0.8 g (50%) of compound 37.

Example B7

Preparation of

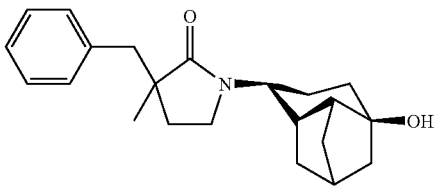

Compound 38

Reaction under $N_2$ atmosphere. A mixture of compound 37 (0.0006 mol) in THF (10 ml) was stirred at −78° C. Sec. butyllithuim 1.3M/hexane (0.0026 mol) was added and the mixture was stirred for 2 hours at −78° C. Iodomethane (0.0012 mol) was added dropwise at −78° C. and the resultant reaction mixture was stirred over the weekend, allowing the temperature to slowly rise from −78° C. to room temperature. The mixture was poured out into an $NH_4Cl$ solution (4 ml). This mixture was extracted with DCM. The separated organic layer was dried through Extrelut. The filtrate was evaporated. The residue was purified by column chromatography over silica gel (Supelco; eluent: DCM/$CH_3OH$ 99/2). The product fractions were collected and the solvent was evaporated, yielding 0.153 g of compound 38.

Example B8

Preparation of

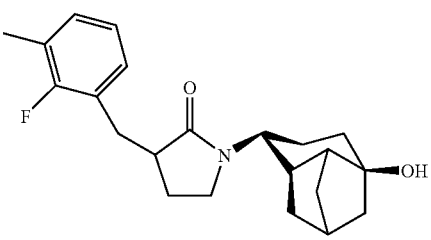

Compound 39

Reaction under $N_2$ atmosphere. A mixture of intermediate 14 (0.005 mol) in THF (50 ml) was stirred at −78° C. Sec. butyllithium 1.3M/hexane (0.013 mol) was added dropwise and the mixture was stirred for 3 hours at −78° C. 1-(bromomethyl)-2-fluoro-3-methyl-benzene (0.01 mol) was added dropwise at −78° C. and the resultant reaction mixture was stirred for one hour at −78° C., then stirred overnight at room temperature. The mixture was poured out into a saturated aqueous $NH_4Cl$ solution. This mixture was extracted with DCM. The separated organic layer was dried, filtered and the solvent evaporated. The residue was purified by column chromatography over silica gel (Biotage; eluent: DCM/$CH_3OH$ 99/1). The product fractions were collected and the solvent was evaporated. The residue (0.4 g) was dissolved in THF. The solvent was evaporated, yielding 0.4 g of compound 39.

Example B9

Preparation of

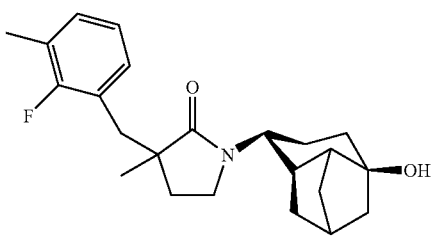

Compound 40

A mixture of compound 39 (0.0011 mol) in THF (25 ml) was stirred under $N_2$ at −78° C. and sec.-butyllithium 1.3M/hexane (0.0022 mol) was added dropwise, then the mixture was stirred for 2 hours at −78° C. and iodomethane (0.005 mol) was added dropwise. The reaction mixture was stirred for 1 hour at −78° C. and then stirred overnight at room temperature. A saturated $NH_4Cl$ solution (5 ml) was added dropwise, then the resulting mixture was stirred for 10 minutes and was extracted with DCM. The organic layer was washed, dried, filtered off and the solvent was evaporated. The residue was purified by column chromatography over silica gel (eluent: $DCM/CH_3OH$ 98/2). The product fractions were collected and the solvent was evaporated. The residue (0.242 g) was dissolved in diethyl ether and then the solvent was evaporated (vacuo) at 80° C., yielding 0.221 g of compound 40.

C. Pharmacological Examples

Example C.1

Enzymatic Assays to Test the Effect of Compounds on 11b-hydroxysteroid dehydrogenase Type 1 and Type 2

The effects of compounds on 11β-HSD1 dependent conversion of cortisone into cortisol (reductase activity) was studied in a reaction mixture containing 30 mM Tris-HCl buffer pH 7.2, 180 μM NADPH, 1 mM EDTA, 2 μM cortisone, 1 μl drug and/or solvent and 11 μg recombinant protein in a final volume of 100 μl.

The effect on the 11β-HSD 1-dehydrogenase activity (conversion of cortisol into cortisone) was measured in a reaction mixture containing 0.1M sodium phosphate buffer pH 9.0, 300 μM NADP, 25 μM cortisol, 1 μl drug and/or solvent and 3.5 μg recombinant protein in a final volume of 100 μl.

The effects on the 11β-HSD2 dependent dehydrogenase activity was studied in a reaction mixture containing 0.1M sodium phosphate buffer pH 7.5, 300 μM NAD, 100 nM cortisol (of which 2 nM is 3H-radio labelled), 1 μl drug and/or solvent and 2.5 μg recombinant protein in a final volume of 100 μl.

All incubations were performed for 45 minutes at 37° C. in a water bath. The reaction was stopped by adding 100 μl acetonitrile containing 20 μg corticosterone as internal standard. After centrifugation, the product formation was analysed in the supernatant by HPLC on a Hypersyl BDS-C18 column using 0.05 mM ammonium acetate/methanol (50/50) as solvent. In all of the aforementioned assays, the drugs to be tested were taken from a stock solution and tested at a final concentration ranging from −$10^{-5}$M to 3·$10^{-9}$M. From the thus obtained dose response curves, the pIC50 value was calculated and scored as follows; Score 1=pIC50 value<5, Score 2=pIC50 value in the range of 5 to 6, Score 3=pIC50 value>6. Some of the thus obtained results are summarized in the table below (in this table NT stands for Not Tested).

Example C2

Cellular Assays to Test the Effect of Compounds on 11b-hydroxysteroid dehydrogenase Type 1 and Type 2

The effects on 11β-HSD1 activity was measured in differentiated 3T3-L1 cells and rat hepatocytes.

Mouse fibroblast 3T3-L1 cells (ATCC-CL-173) were seeded at a density of 16500 cells/ml in 12 well plates and grown for 7 days in DMEM medium (supplemented with 10% heat inactivated foetal calf serum, 2 mM glutamine and 25 mg gentamycin) at 37° C. in a humidified 5% $CO_2$ atmosphere. Medium was refreshed twice a week. Fibroblasts were differentiated into adipocytes at 37° C. in a 5% $CO_2$ humidified atmosphere in growth medium containing 2 μg/ml insulin, 55 μg/ml IBMX and 39.2 μg/ml dexamethasone.

Primary hepatocytes from male rats were seeded on BD-Biocoat Matrigel matrix multiwell plates at a density of 250000 cells/well and incubated for 10 days at 37° C. in a 5% $CO_2$ humidified atmosphere in DMEM-HAM's F12 medium containing 5% Nu-serum, 100 U/ml penicillin, 100 μg/ml streptomycin, 0.25 μg/ml amphotericin B, 50 μg/ml gentamycin sulfate, 5 μg/ml insulin and 392 ng/ml dexamethasone. Medium was refreshed 3 times a week.

Following a 4 hour pre-incubation with test compound, 0.5 μCi $^3$H-cortisone or dehydrocorticosterone, was added to the cultures. One hour later, the medium was extracted on Extrelut$^3$-columns with 15 ml diethyl ether and the extract was analysed by HPLC as described above.

The effects on 11β-HSD2 activity was studied in HepG2 and LCC-PK1-cells HepG2-cells (ATCC HB-8065) were seeded in 12 well plates at a density of 100,000' cells/ml and grown at 37° C. in a humidified 5% $CO_2$ atmosphere in MEM-Rega-3 medium supplemented with 10% heat inactivated foetal calf serum, 2 mM L-glutamine and sodium bicarbonate). Medium was refreshed twice a week.

Pig kidney cells (LCC-PK1, ATCC CRL-1392) were seeded at a density of 150,000 cells/ml in 12 well plates and grown at 37° C. in a humidified 5% $CO_2$ atmosphere in Medium 199 supplemented with Earls modified salt solution, 100 U/ml penicillin, 100 μg/ml streptomycin and 10% foetal calf serum. Medium was refreshed twice a week. Twenty four hours prior to the onset of the experiment, medium was changed by medium containing 10% charcoal stripped foetal calf serum.

Following a 4 hour pre-incubation with test compound, 0.5 μCi $^3$H-cortisol or corticosterone, was added to the cultures. One hour later, the medium was extracted on Extrelut$^3$-columns with 15 ml diethyl ether and the extract was analysed by HPLC as described above.

As for the enzymatic assays, the compounds to be tested were taken from a stock is solution and tested at a final concentration ranging from −$10^{-5}$M to 3·$10^{-9}$M. From the thus obtained dose response curves, the pIC50 value was calculated and scored as follows; Score 1=pIC50 value<5, Score 2=pIC50 value in the range of 5 to 6, Score 3=pIC50 value>6. Some of the thus obtained results are summarized in the table below (in this table NT stands for Not Tested).

| Compound Number | [C1] HSD1-prot Reduct Score | [C1] HSD2-prot Dehydro Score | [C2] HSD1 cellular 3T3-L1 Score | [C2] HSD2 cellular HepG2 Score |
|---|---|---|---|---|
| 3 | 3 | NT | 3 | 1 |
| 4 | NT | NT | 3 | NT |
| 5 | NT | NT | 3 | NT |
| 6 | NT | NT | 3 | NT |
| 7 | NT | NT | 3 | NT |
| 1 | 3 | NT | 3 | 1 |
| 8 | 3 | NT | 3 | 1 |
| 9 | NT | NT | 1 | NT |
| 10 | NT | NT | 2 | NT |
| 11 | NT | NT | 3 | NT |
| 12 | NT | NT | 1 | NT |
| 13 | 3 | NT | 1 | 1 |
| 14 | 3 | NT | 3 | 1 |
| 15 | NT | NT | 1 | NT |
| 16 | 3 | NT | 3 | 1 |
| 17 | NT | NT | 3 | NT |
| 18 | NT | NT | 1 | NT |
| 19 | NT | NT | 3 | NT |
| 20 | NT | NT | 3 | NT |
| 2 | 3 | NT | 3 | 1 |
| 21 | NT | NT | 3 | NT |
| 22 | NT | NT | 1 | NT |
| 23 | NT | NT | 1 | NT |
| 24 | NT | NT | 1 | NT |
| 25 | NT | NT | 3 | NT |
| 26 | NT | NT | 3 | NT |
| 27 | NT | NT | 1 | NT |
| 28 | NT | NT | 1 | NT |
| 29 | 3 | NT | 3 | 2 |
| 30 | 3 | NT | 3 | 1 |
| 31 | NT | NT | 1 | NT |
| 32 | NT | NT | 3 | NT |
| 33 | NT | NT | 3 | NT |
| 34 | NT | NT | 1 | NT |
| 35 | NT | NT | 3 | NT |
| 36 | NT | NT | 3 | NT |
| 37 | NT | NT | 3 | 1 |
| 38 | NT | 1 | 3 | NT |
| 39 | NT | 1 | 3 | NT |
| 40 | NT | 1 | 3 | 2 |

D. Composition Examples

The following formulations exemplify typical pharmaceutical compositions suitable for systemic or topical administration to animal and human subjects in accordance with the present invention.

"Active ingredient" (A.I.) as used throughout these examples relates to a compound of formula (I) or a pharmaceutically acceptable addition salt thereof.

Example D.1

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-1-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in $CH_2Cl_2$ (150 ml). Then there were added $CH_2Cl_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the whole was homogenated. The tablet cores were coated with the thus obtained mixture in a coating apparatus.

The invention claimed is:

1. A compound having the formula

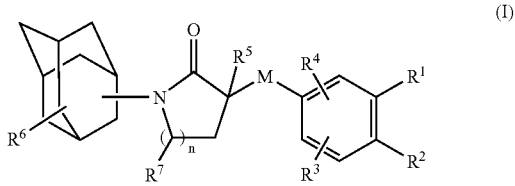

(I)

or a pharmaceutically acceptable addition salt or a stereochemically isomeric form thereof, wherein n is 1 or 2;

M represents a direct bond or a $C_{1-3}$alkyl linker optionally substituted with one or two substituents selected from $C_{1-4}$alkyl, $C_{1-3}$alkyloxy-$C_{1-4}$alkyl-, hydroxy-$C_{1-4}$alkyl-, hydroxy, $C_{1-3}$alkyloxy- or phenyl-$C_{1-4}$alkyl-;

$R^1$ and $R^2$ each independently represent hydrogen, halo, cyano, hydroxy, $C_{1-4}$alkyl optionally substituted with halo, $C_{1-4}$alkyloxy-optionally substituted with one or where possible two or three substituents selected from hydroxy, $Ar^1$ and halo;

$R^3$ represents hydrogen, halo, $C_{1-4}$alkyl, $C_{1-4}$alkyloxy-, cyano or hydroxy;

$R^4$ represents hydrogen, halo, $C_{1-4}$alkyl, hydroxy, cyano or $C_{1-4}$alkyloxy-optionally substituted with one or where possible two or three substituents selected from hydroxy and halo;

$R^5$ represents hydrogen, $C_{1-4}$alkyl or $Ar^2$—$C_{1-4}$alkyl-;

$R^6$ represents hydrogen, hydroxy, halo, $C_{1-4}$alkyl or $C_{1-4}$alkyloxy-;

$R^7$ represents hydrogen or $R^7$ and $R^5$ taken together with the carbon atom to which they are attached from a —$C_2$-alkyl-linker;

$Ar^1$ and $Ar^2$ each independently represent phenyl or naphthyl wherein said phenyl and naphthyl are optionally substituted with $C_{1-4}$alkyl, $C_{1-4}$alkyloxy-, or phenyl-$C_{1-4}$ alkyl.

2. A compound having the formula

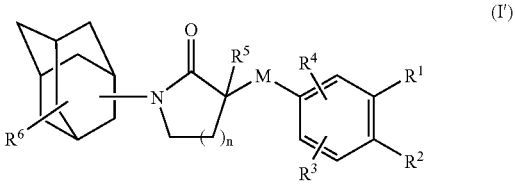

(I')

or a pharmaceutically acceptable addition salt or a stereochemically isomeric form thereof, wherein n is 1 or 2;

M represents a $C_{1-3}$alkyl linker optionally substituted with one or two substituents selected from $C_{1-4}$alkyl, $C_{1-3}$alkyloxy-$C_{1-4}$alkyl-, hydroxy-$C_{1-4}$alkyl-, hydroxy, $C_{1-3}$alkyloxy- or phenyl-$C_{1-4}$alkyl-;

$R^1$ and $R^2$ each independently represent hydrogen, halo, cyano, hydroxy,
  $C_{1-4}$alkyl optionally substituted with halo,
  $C_{1-4}$alkyloxy-optionally substituted with one or where possible two or three substituents selected from hydroxy, $Ar^1$ and halo;

$R^3$ represents hydrogen, halo, $C_{1-4}$alkyl, $C_{1-4}$alkyloxy-, cyano or hydroxy;

$R^4$ represents hydrogen, halo, $C_{1-4}$alkyl, hydroxy, cyano or $C_{1-4}$alkyloxy-optionally substituted with one or where possible two or three substituents selected from hydroxy and halo;

$R^5$ represents hydrogen, $C_{1-4}$alkyl or $Ar^2$—$C_{1-4}$alkyl-;

$R^6$ represents hydrogen, hydroxy, halo, $C_{1-4}$alkyl or $C_{1-4}$alkyloxy-;

$Ar^1$ and $Ar^2$ each independently represent phenyl or naphthyl wherein said phenyl and naphthyl are optionally substituted with $C_{1-4}$alkyl, $C_{1-4}$alkyloxy-, or phenyl-$C_{1-4}$ alkyl.

3. A compound according to claims 1 or 2 wherein;

n is 1 or 2;

M represents a $C_1$-linker optionally substituted with $C_{1-4}$alkyl, hydroxy or hydroxy-$C_{1-4}$alkyl;

$R^1$ represents hydrogen, hydroxy, cyano, halo, $C_{1-4}$alkyl, $C_{1-4}$alkyloxy-, $C_{1-4}$alkyl substituted with one or where possible two or three halo substituents or $R^1$ represents $C_{1-4}$alkyloxy substituted with halo;

$R^2$ represents hydrogen, halo, $C_{1-4}$alkyl or $C_{1-4}$alkyloxy-optionally substituted with one or where possible two or three halo substituents;

$R^3$ represents hydrogen, halo, $C_{1-4}$alkyl, $C_{1-4}$alkyloxy- or $C_{1-4}$alkyl substituted with one or where possible two or three halo substituents;

$R^4$ represents hydrogen, halo or $C_{1-4}$alkyl;

$R^5$ represents hydrogen, $C_{1-4}$alkyl or $Ar^2$—$C_{1-4}$alkyl;

$R^6$ represents hydrogen or hydroxy;

$Ar^2$ represents phenyl optionally substituted with $C_{1-4}$alkyloxy-.

4. A compound according to claims 1 or 2 wherein;

n is 1 or 2;

M represents a $C_1$-linker;

$R^1$ and $R^2$ represent hydrogen, $C_{1-4}$alkyl or $C_{1-4}$alkyloxy;

$R^3$ represents hydrogen or $C_{1-4}$alkyloxy;

$R^4$ represents hydrogen or halo;

$R^5$ represents hydrogen or $C_{1-4}$alkyl;

$R^6$ represents hydrogen or hydroxy.

5. A compound as claimed in claim 1 wherein the compound is selected from the group consisting of;

3-[(3,5-dimethoxyphenyl)methyl]-1-tricyclo[3.3.1.1$^{3,7}$]dec-2-yl-2-pyrrolidinone;

3-[(4-methylphenyl)methyl]-1-tricyclo[3.3.1.1$^{3,7}$]dec-2-yl-2-pyrrolidinone;

3-[(2-fluoro-3-methylphenyl)methyl]-3-methyl-1-tricyclo[3.3.1.1$^{3,7}$]dec-2-yl-2-pyrrolidinone;

3-[(3-methoxyphenyl)methyl]-3-methyl-1-tricyclo[3.3.1.1$^{3,7}$]dec-2-yl-2-pyrrolidinone;

3-Benzyl-1-(5-hydroxy-tricyclo[3.3.1.13,7]dec-2-yl)-pyrrolidin-2-one;

3-Benzyl-1-(5-hydroxy-tricyclo[3.3.1.13,7]dec-2-yl)-3-methyl-pyrrolidin-2-one;

3-(2-Fluoro-3-methyl-benzyl)-1-(5-hydroxy-tricyclo[3.3.1.13,7]dec-2-yl)-pyrrolidin-2-one; and 3-(2-Fluoro-3-methyl-benzyl)-1-(5-hydroxy-tricyclo[3.3.1.13,7]dec-2-yl)-3-methyl-pyrrolidin-2-one;

or a pharmaceutically acceptable addition salt or a stereochemically isomeric form thereof.

6. A pharmaceutical composition comprising a pharmaceutically acceptable carrier and, as active ingredient, a compound as described in claim 1.

7. A process of preparing a pharmaceutical composition as defined in claim 6, characterized in that, a pharmaceutically acceptable carrier is intimately mixed with a compound as described in claim 1.

* * * * *

UNITED STATES PATENT AND TRADEMARK OFFICE
CERTIFICATE OF CORRECTION

PATENT NO. : 7,687,644 B2 Page 1 of 1
APPLICATION NO. : 11/632195
DATED : March 30, 2010
INVENTOR(S) : Jaroskova et al.

It is certified that error appears in the above-identified patent and that said Letters Patent is hereby corrected as shown below:

Column 36
Line 34-35, delete "as defined in claim 6".

Signed and Sealed this

Twelfth Day of October, 2010

David J. Kappos
*Director of the United States Patent and Trademark Office*